United States Patent
Tani

(10) Patent No.: US 7,993,321 B2
(45) Date of Patent: Aug. 9, 2011

(54) DISPOSABLE DIAPER

(75) Inventor: Koichiro Tani, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 1507 days.

(21) Appl. No.: 10/673,258

(22) Filed: Sep. 30, 2003

(65) Prior Publication Data

US 2004/0082931 A1    Apr. 29, 2004

(30) Foreign Application Priority Data

Sep. 30, 2002  (JP) .................................. 2002-287569
May 1, 2003    (JP) ................................. 2003-126651

(51) Int. Cl.
*A61F 13/15* (2006.01)
*A61F 13/20* (2006.01)
(52) U.S. Cl. ......... 604/389; 604/386; 604/391; 604/394
(58) Field of Classification Search .................. 604/386, 604/389–391, 394
See application file for complete search history.

(56) References Cited

U.S. PATENT DOCUMENTS

| 3,848,594 | A | * | 11/1974 | Buell ............................. 604/390 |
| 5,399,219 | A | | 3/1995 | Roessler et al. |
| 6,004,306 | A | * | 12/1999 | Robles et al. ............ 604/385.21 |
| 2003/0109843 | A1 | | 6/2003 | Gibbs |

FOREIGN PATENT DOCUMENTS

| JP | 9-506535 | 6/1997 |
| JP | 10-510199 | 10/1998 |
| JP | 3162592 | 2/2001 |
| JP | 2002-209936 | 7/2002 |
| JP | 2003-153951 | 5/2003 |
| WO | 95-16425 | 6/1995 |
| WO | 96/35402 | 11/1996 |
| WO | 02/05739 | 1/2002 |

OTHER PUBLICATIONS

Notice of Reasons for Rejection (Japan Patent Office) for JP 2003-126651 dated May 8, 2007.

* cited by examiner

*Primary Examiner* — Melanie J Hand
(74) *Attorney, Agent, or Firm* — Lowe, Hauptman, Ham & Berner, LLP

(57) ABSTRACT

A disposable diaper includes a diaper body and a pair of side flaps each fixed to the diaper body at a fixing part and at least a joint part. The diaper body has transversely opposite side parts, each of which has opposite first and second end parts. The fixing parts and joint parts are located at the first end parts of the disposable diaper. Each fixing part is located inwardly of the respective joint part as seen in the width direction of the diaper body. Each side flap has an inner end part fixed to the diaper body and an outer end part to which a fastener is fixed.

19 Claims, 16 Drawing Sheets

DISPOSABLE DIAPER

The entire disclosure of Japanese patent application No. 2002-287569 filed with the Japan Patent Office on Sep. 30, 2002 and Japanese patent application No. 2003-126651 filed with the Japan Patent Office on May 1, 2003 is incorporated herein by reference.

FIELD OF THE INVENTION

The present invention relates to a taped disposable diaper and, more specifically, relates to a disposable diaper where tensile force by fasteners installed on outer end parts of a pair of side flaps positioned along a side end part in the width direction of a diaper body is effectively distributed around the waist direction and around the leg directions.

BACKGROUND ART

A disposable diaper in general use includes a diaper body having a top sheet, a back sheet and an absorbent body between a top sheet and a back sheet; a pair of side flaps positioned around the waist of the disposable diaper along a side end part in the width direction of a diaper body; and a pair of fasteners installed on an outer end part of each side flap part. The absorbent body is positioned to cover the groin region of a wearer when the disposable diaper is worn.

The above disposable diaper is worn by fitting the diaper body to the wearer in a usual method upon use, and is attached to the wearer by fixedly attaching the fastener installed on the side flap part of the diaper, around the waist on the opposite side. In this disposable diaper, it is required to fit both around the waist and legs of the wearer when the disposable diaper is worn by the wearer and to prevent liquid leakage from the leg parts and waist part while wearing a diaper.

However, for a disposable diaper where one fastener is installed on the outer end of the side flap, it has been difficult that the tensile force of the fastener is effectively concentrated around both the waist and legs of the wearer when the diaper body is worn by the wearer. That is, when the disposable diaper is attached to completely fit around the waist of the wearer, a gap remains around the legs and liquid leakage occurs from the leg region during use. Also, on the contrary, a difficulty exists in that the diaper cannot fit around the waist of the wearer because a gap remains around the waist of the wearer when attached to completely fit around the legs of the wearer.

In order to solve such problems, for example, there is a disposable diaper as described in Japanese Patent No. 3162592.

This Japanese Patent No. 3162592 installed a stress relaxation section with less tensile stress than that in surrounding parts in an area except the surrounding parts of an ear part, in the disposable diaper having one fastener installed on the area except the surrounding parts of the ear part, a pair of end edges, a centerline in a longitudinal direction and a centerline in a crosswise direction. An area extending from a part of one end edge of the disposable diaper, which is an intersecting point between the centerline in the longitudinal direction of the disposable diaper and the one end edge to the ear-part outer end part located on the side of the one end edge from an intersecting point where a first line in contact with the stress relaxation section comes into contact with the outer end part of the ear part, is provided as a first area. An area extending from a part of the ear end edge at the side of the centerline in the crosswise direction of the disposable diaper to the ear-part outer end part located on the side of the crosswise centerline from a point where a second line in contact with the stress relaxation section comes into contact with the outer end part of the ear part, is provided as a second area. Provided is the disposable diaper having a fastener attached to a location that can effectively and directly concentrate the tensile force of the fastener around the legs and waist of the disposable diaper by attaching the fastener to overlap on at least a part of the first side edge area and a part of the second side edge area (Japanese Patent No. 3162592).

However, in such a conventional disposable diaper, the stress relaxation section with less tensile stress than the surrounding parts is poor in fitness to a body of the wearer and a gap remains. Also, installing an emboss, slit, aperture or the like which is a means of stress relaxation has undesirable effects on the wearer, such as bad contact with skin and poor aesthetics. Also, inconvenience exists such that the first side edge area where the fastener is not joined is defectively turned up while wearing a diaper since the stress applied to the fastener upon wearing is not conveyed.

DISCLOSURE OF THE INVENTION

The present invention has been made in view of the above problem and an object thereof is to provide a disposable diaper capable of distributing tensile force by fasteners, which are provided on outer end parts of a pair of side flaps positioned along a side end part in the width direction of the diaper body, effectively around the waist peripheral direction and leg directions.

In order to resolve the above problem, in the present invention, it has been found that the tensile force of a fastener of a disposable diaper can be effectively and directly concentrated around the legs and waist by partially joining and fixing a side edge upper end and a side edge lower end of a side flap, near a side flap fixing part in addition to the side flap fixing part where the side flap is fixed to the diaper body when a pair of side flaps are fixed to the diaper body.

More specifically, the present invention provides the following:

(1) A disposable diaper comprising: a diaper body having a top sheet, a back sheet, and an absorbent body enclosed between said top sheet and said back sheet; a pair of side flaps fixed to said diaper body at side flap fixing parts and joint parts, wherein said diaper body has a pair of parallel side end parts in a longitudinal direction of said diaper body; and a pair of fasteners, wherein each of said side end part has a first end part and a second end part which is located at an opposite side of said first end part; wherein said side flap fixing parts and joint parts are located at said first end part of said disposable diaper, and wherein said side flap fixing parts are located on a side inner toward said diaper body than said joint parts along the width direction of said diaper body; and wherein each of said side flap has an inner end part being disposed on an inner side to said diaper body along the width direction of said diaper body and an outer end part being disposed on an outer side to said diaper body along the width direction of said diaper body, and each of said fasteners is fixed to said outer end part of each of said side flap.

According to this aspect of the invention, it is preferable that the side flap is fixed by joining with heat seal, sonic seal, hot melt adhesive or the like such that one inner end part is on an extended line of the "leg gathers" of the diaper body or at the side inner than the "leg gathers" in the width direction of the diaper body (near a center line L-L' of the diaper body in FIG. 1). Also, at the side outer than this side flap fixing part, in the width direction of the diaper body, it is preferable that a side edge upper part and a side edge lower part of the side flap are joined to at least one site at the outside end part of the diaper body or a vicinity thereof by a thermal method such as heating and/or compression with heat seal, sonic seal, hot melt adhesive or the like. And it is preferable that the fastener is installed on the other outer end part of the side flap. The diaper body and the side flap is integrated by the side flap fixing part by making such a configuration. Also, because of having sites partially joined at the side outer than this side flap fixing part, when the fastener installed on the side flap is pulled to the outside, the pulling force is divided into tensile force exerted to a joint part of the side edge upper area of the side flap and tensile force exerted to a joint part of the side edge lower area of the side flap, and then respective divisional tensile forces of the disposable diaper pull around the waist and legs. At that time, since the divisional forces vary by appropriately setting a divisional ratio of the tensile force, when a wearer wears the disposable diaper, respective divisional tensile forces pull around the waist and legs, and the diaper fits around both the waist and legs of the wearer. The division of the pulling force can be appropriately set by changing the location of the fastener installed on the side flap and lengths of the joint parts. That is, the force exerted to the side edge upper end area of the side flap and the force exerted to the side edge lower end area of the side flap are nearly equally distributed by installing the fastener at a center in the vertical direction of the side flap. However, when the location where the fastener is installed becomes the site upper than the center, the divisional ratio of the puling force exerted to the side edge upper end area of the side flap becomes larger. Conversely, as it becomes a lower site, the divisional ratio of the pulling force exerted to the side edge lower end area of the side flap becomes larger. Also, the higher the length ratio of upper to lower joint parts is, the greater the divisional ratio of upper to lower divisional forces of the pulling force is. Additionally, by changing the fixing location of the joint part along the width direction of the diaper, the shorter the distance between the fastener and the fixing location is, the greater the divisional ratio of the pulling force is. The divisional ratio of the pulling force depends on a relative position of the upper or lower joint part to the fastener position such that the ratio of the upper tensile force to the lower tensile force may be higher if the distance between the upper joint part and the fastener becomes shorter. Thus, the set location of the fastener, and the length or location of the joint parts can be appropriately set depending on the required purpose.

Also, the side flap comprises non-woven fabric, and may be either elastic or non-elastic. However, it is preferable to have elasticity in terms of being capable of adjusting around the waist when the disposable diaper is worn.

(2) The disposable diaper as described in (1), wherein said first end part of said diaper body and said inner end part of said side flap are overlapped.

According to this aspect of the invention, since the first end part of the diaper body and the inner end part of the side flap are overlapped, by pulling the fastener fixed to the side flap, the first end part of the diaper body is also pulled, and therefore the tensile force can be effectively and directly concentrated around the waist and legs. Thus, fitness around the waist and legs of the wearer can be improved.

(3) The disposable diaper as described in (1) or (2), wherein said joint part comprises a first joint part located at an upper part of said inner end part of said side flap and a second joint part located at a lower part of said inner end part of said side flap, and wherein said first joint part and said second joint part have a same length.

According to this aspect of the invention, since the first joint part located at the upper part of the inner end part of the side flap and the second joint part located at the lower part of the inner end part of the side flap are the same in the length, the tensile force of the fastener fixed to the side flap is nearly equally distributed to the first and second joint parts. Thus, since the distribution of tensile force renders evenly, fitness around the waist and legs of the wearer can be improved.

(4) The disposable diaper as described in any of (1) to (3), wherein said side flap comprises an elastic sheet and a non-woven fabric.

According to this aspect of the invention, since the side flap has elasticity (including resiliency) and the dimension around the waist can be adjusted when the disposable diaper is worn, it is possible to further fit around the waist of the wearer.

(5) The disposable diaper as described in any of (1) to (4), wherein said fastener is positioned at a at a substantial center in the vertical direction of an outer end part of said side flap.

According to this aspect of the invention, the fastener is located at a substantial center in the vertical direction of the outer end part of said side flap. Thus, when the fastener is pulled, the tensile force is distributed to the side edge upper end area and the side edge lower end area of the side flap based on the difference of lengths between the first joint part and the second joint part, an effective length between the first joint part and the fastener and an effective length between the second joint part and the fastener.

(6) The disposable diaper as described in any of (1) to (5), wherein said joint part comprises a first joint part located at the side edge upper end area of the side flap and a second joint part located at the side edge lower end area of the side flap, and wherein the respective joint parts have a same length.

According to this aspect of the invention, the joint parts of the side flap and the diaper body at the side edge upper end area and the side edge lower end area of the side flap have the same length. That is, when the fastener is pulled, the tensile force is substantially equally distributed to the side edge upper end area and the side edge lower end area of the side flap, the areas around the waist and legs are substantially equally pulled, and thus, the waist portion and leg portions of the disposable diaper fit around the waist and legs of the wearer. Since the distributed forces can be changed in the distribution ratio by changing the length of the joint part, it becomes possible to appropriately change the tensile forces around the waist and legs. Here, the length of the joint part means the length of the joint part in the vertical direction (longitudinal direction of the diaper body).

(7) The disposable diaper as described in any of (1) to (6), wherein said joint part and said side flap fixing part are joined and fixed by a thermal method.

According to this aspect of the invention, it is preferable that joining and fixing of the diaper body and the side flap is performed by a thermal method such as heating, pressure bonding, e.g., heat seal, sonic seal, hot melt adhesive or the like. Thus, the method is excellent in workability and productivity since the joint can be performed in a short period of time, and the work is easy.

(8) The disposable diaper as described in any of (1) to (7), wherein said fastener comprises a fastening member and a fastening tape substrate.

(9) The disposable diaper as described (1) or (2), wherein said joint part comprises a first joint part located at an upper part of said inner end part of said side flap and a second joint part located at a lower part of said inner end part of said side flap, and wherein a length of said first joint part is shorter than a length of said second joint part.

According to this aspect of the present invention, said joint part comprises a first joint part located at an upper part of said inner end part of said side flap and a second joint part located at a lower part of said inner end part of said side flap, and wherein a length of said first joint part is shorter than a length of said second joint part. Therefore, when the fastener is pulled, the tensile force applied to the fastener is divided into the force interlocking with the side edge upper end area and the force interlocking with the side edge lower end area, and the force interlocking with the side edge lower end area is stronger than the force interlocking with the side edge upper end area. Consequently, areas around the legs are more effectively and intensively pulled than areas around the waist, thus resulting in a better fitness at areas around the legs of the wearer.

(10) The disposable diaper according to (1) or (2), wherein said joint part comprises a first joint part located at an upper part of said inner end part of said side flap and a second joint part located at a lower part of said inner end part of said side flap, and wherein a length of said first joint part is longer than a length of said second joint part.

According to this aspect of the present invention, said joint part comprises a first joint part located at an upper part of said inner end part of said side flap and a second joint part located at a lower part of said inner end part of said side flap, and wherein a length of said first joint part is longer than a length of said second joint part. Therefore, when the fastener is pulled, the tensile force applied to the fastener is divided into the force interlocking with the side edge upper end area and the force interlocking with the side edge lower end area, and the force interlocking with the side edge upper end area is stronger than the force interlocking with the side edge lower end area. Consequently, areas around the waist are more effectively and intensively pulled than areas around the legs, thus resulting in a better fitness at areas around the waist of the wearer.

As mentioned above, varying the length of the first joint part located at the upper part of said inner end part of said side flap and the second joint part located at the lower part of said inner end part of said side flap allows to control the tensile forces interlocking with areas around the waist and with areas around the legs.

(11) The disposable diaper according to any one of (1) to (10), wherein said joint part comprises a first joint part located at an upper part of said inner end part of said side flap and a second joint part located at a lower part of said inner end part of said side flap.

(12) The disposable diaper according to any one of (1) to (3) and (5) to (11), wherein said side flap comprises an elastic sheet.

According to this aspect of the invention, since the side flap has elasticity, the dimension around the waist can be adjusted when the disposable diaper is worn. Therefore, it is possible to further fit around the waist of the wearer.

(13) The disposable diaper according to (4), wherein said non-woven fabric is elastic.

(14) A method for adjusting fitness around a waist and legs when a disposable diaper is worn, comprising the step of: joining a diaper body of the disposable diaper with another member by a joint part at a prescribed position.

According to this aspect of the present invention, when the disposable diaper is pulled, the tensile force is acted on the joint part where the diaper body is joined with another member, and then areas around the waist and areas around the leg are effectively pulled. For example, when another member is a side flap which is provided in the end part in the longitudinal direction of the diaper body and when the joint part is located at an upper part of an inner end part, areas around the waist is more pulled than areas around the legs, and therefore, areas around the waist fits more than areas around the legs. When the joint part is located at a lower part of an inner end part, areas around the legs is more pulled than areas around the waist, and therefore, areas around the legs fits more than areas around the waist. On the other hand, when the joint part is not present, the tensile force is evenly distributed over an upper part of the inner end part and a lower part of the inner end part of the side flap, and therefore, areas around the waist and areas around the legs are evenly pulled. As a result, the fitness around the waist is substantially the same as the fitness around the legs. As aforementioned, the presence of the joint part for joining another member allows adjust fitness around the waist and legs.

(15) A method for adjusting fitness around a waist and legs when a disposable diaper is worn, by adjusting a length of a first joint part located at a side edge upper end area of a side flap and a second joint part located at a side edge lower end of the side flap, in the disposable diaper wherein an inner end part of the side flap is fixed to an inner side end part of the diaper body, and either or both the side edge upper end area and the side edge lower end area of the side flap are joined to the diaper body at an outer side end part from said inner side end part of the diaper body.

According to this aspect of the invention, when the fastener is pulled, the tensile force is distributed to the side edge upper end area of the side flap and the side edge lower end area of the side flap, respectively, via joint parts thereof. The force distributed to the side edge upper end area of the side flap pulls around the waist and that to the side edge lower end area pulls around the legs, respectively. Accordingly, when the disposable diaper is worn, fitness around the waist and legs of a wearer can be obtained.

(16) A method for adjusting fitness around a waist and legs when a disposable diaper is worn, by adjusting a width of a first joint part located at a side edge upper end area of the side flap and a second joint part located at a side edge lower end of the side flap, in the disposable diaper wherein an inner end part of the side flap is fixed to an inner side end part of the diaper body, and either or both the side edge upper end area and the side edge lower end area of the side flap are joined to the diaper body at an outer side end part from said inner side end part of the diaper body.

According to this aspect of the invention, when the fastener is pulled, the tensile force is distributed to the first joint part located at the side edge upper end area of the side flap and the second first joint part located at the side edge lower end area of the side flap, respectively. The forces distributed from the tensile force pull the waist and legs, respectively. The distribution or division ratio of the tensile force depends on the length of the joint parts. That is, the longer the length of either joint part is, the greater the distribution ratio is with the joint part of the longer length. Therefore, when fitness around the waist needs to be increased, the length of the first joint part located at the side edge upper end area of the side flap may be made longer than that of the second first joint part located at the side edge lower end area of the side flap, whereby the ratio of tensile force distributed to the first joint part becomes higher, and the force to pull around the waist increases. In this manner, fitness around the waist and legs can be set appropriately.

(17) A method for adjusting fitness around a waist and legs when a disposable diaper is worn, by adjusting respective positions to which a first joint part located at a side edge upper end area of a side flap and a second joint part located at a side edge lower end of the side flap are fixed, in the disposable diaper wherein an inner end part of the side flap is fixed to an inner side end part of the diaper body, and either or both the side edge upper end area and the side edge lower end area of the side flap are joined to the diaper body at an outer side end part from said inner side end part of the diaper body.

According to this aspect of the invention, when the fastener is pulled, the tensile force is distributed to the first joint part located at the side edge upper end area of the side flap and the second first joint part located at the side edge lower end area of the side flap, respectively. The forces distributed from the tensile force pull around the waist and legs, respectively. The distribution of the tensile force depends on the positions of the joint parts. That is, the shorter the distance between the fastener and either joint part is, the greater the ratio of distributed force to the joint part is. Therefore, by typically changing the position of the first joint part located at the side edge upper end area of the side flap and the position of the second first joint part located at the side edge lower end area of the side flap, the ratio of tensile force distributed to the first joint part changes, and the force to pull the waist also changes. In this manner, the fitness around the waist and legs can be set appropriately.

PREFERABLE EMBODIMENTS OF THE INVENTION

Figure 1:
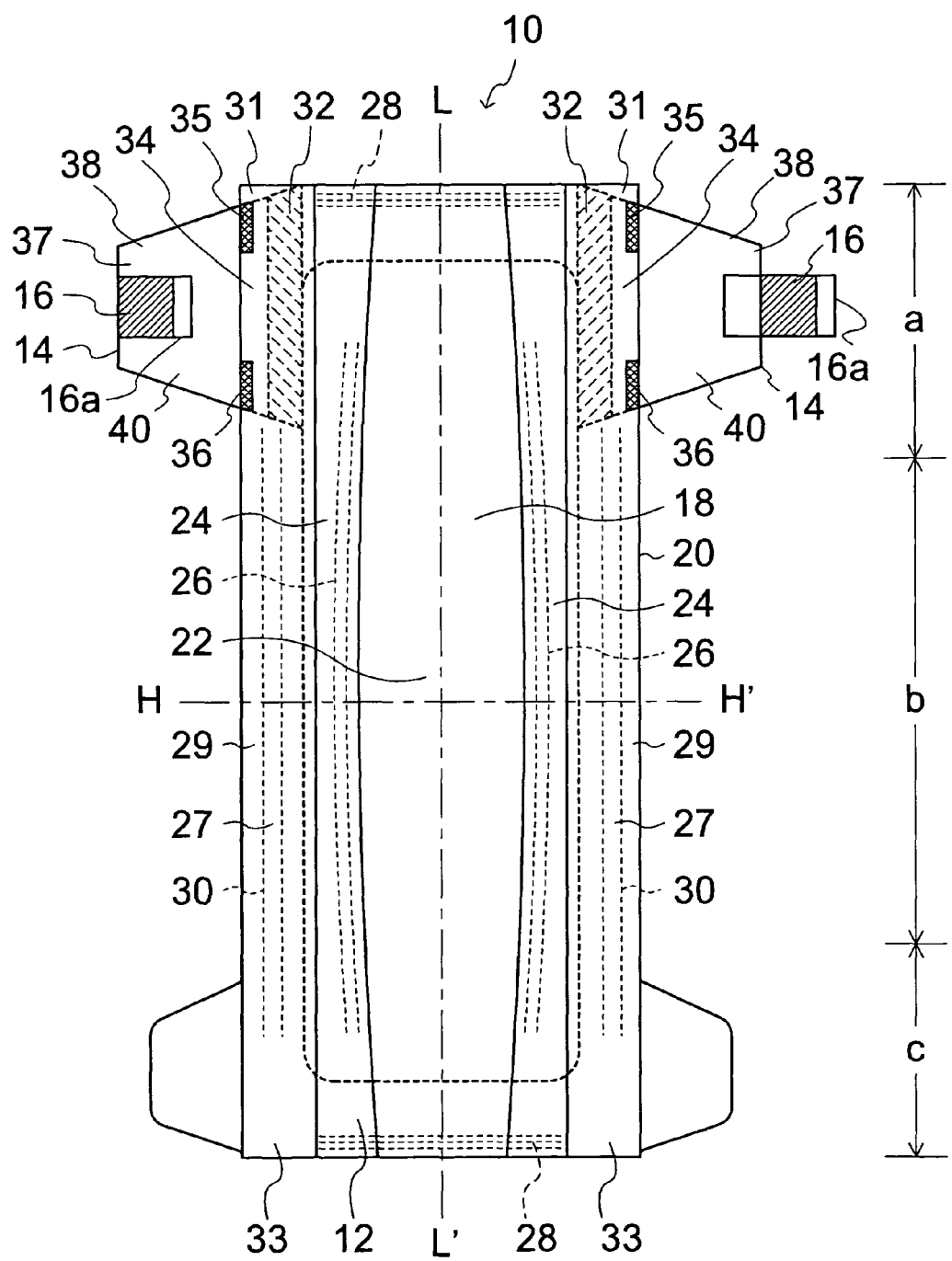
FIG. 1 is a developed view of a disposable diaper according to the first embodiment of the present invention.

Hereinafter, embodiments of the present invention are described by referring to the drawings.

Figure 2:
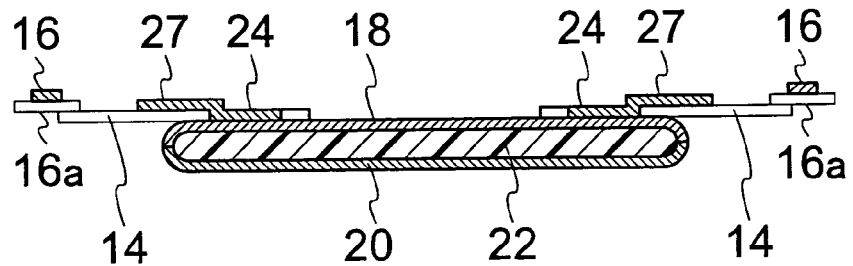
FIG. 2 is a sectional view of the disposable diaper according to the first embodiment of the present invention.

FIG. 1 shows a developed view of the disposable diaper according to the first embodiment of the present invention. This disposable diaper has a first waist area "a", a groin area "b", and a second waist area "c". FIG. 2 shows a sectional view of the disposable diaper along H-H' line in FIG. 1.

The above disposable diaper 10 comprises a diaper body 12, a pair of side flaps 14 extending in the width direction of the diaper body 12 (the H-H' direction in the drawing) in the vicinity of a longitudinal direction end part at the first waist area "a", and fasteners installed on an outer end part 37 of each side flap 14. This fastener comprises a fastening tape substrate 16*a* fixed to the side flap 14 and a fastening member 16 installed on the fastening tape substrate 16*a*.

The diaper body 12 comprises a liquid permeable top sheet 18 which comes into contact with the skin of a wearer, a liquid impermeable back sheet 20 which is provided on the garment side, an absorbent body 22 enclosed by these sheets with a whole shape being approximately rectangular and hourglass-formed, steric gathers 24 installed on a top sheet face at nearly both sides of this absorbent body 22, elastic members 26 positioned along the longitudinal direction (L-L' direction) of the diaper body 12, which impart elasticity to the steric gathers 24, and elastic members 28 positioned, along the width direction of the diaper body 12, at the end part in the longitudinal direction of the diaper body, which impart elasticity to the first waist area a and the second waist area c. The top sheet 18 and the back sheet 20 have greater length and width than the absorbent body 22. The diaper body 12 has a pair of side end parts 29 parallel to the longitudinal direction comprising a first end part 31 and a second end part 33, and forms leg gathers 27 at the groin part area "b" of the side end part 29. Elastic members 30 are positioned to impart elasticity to these leg gathers 27.

Also, the side flap 14 is not a member continuous with the diaper body 12, and is joined as another member at a ventral side or a dorsal side of the first end part 31 of the diaper body 12.

The side flap 14 is fixed to the diaper body 12 at a side flap fixing part 32. Further, the side flap 14 is joined to the diaper body 12 at two sites, a first joint part 35 located at an upper part of the inner end part 34 and a second joint part 36 located at a lower part of the inner end part 34. The first joint part 35 and the second joint part 36 are installed apart in the longitudinal direction (L-L' direction) of the disposable diaper 10.

The side flap fixing part 32, the first joint part 35 and the second joint part 36 which join the side flap 14 and the diaper body 12 are joined between the top sheet 18 and the back sheet 20 by a thermal method such as heating/pressure bonding with heat seal, sonic seal, hot melt adhesive, or the like.

The side flap fixing part 32 is placed so as to locate at an inner site of the inner end part 34 of the side flap 14 in the width direction. On the other hand, the first joint part 35 and the second joint part 36 are placed at an outer site of the inner end part 34 in the width direction and at an outer site than an extended line of the leg gathers 27, in the width direction of the diaper body 12, apart from the side flap fixing part 32. It is preferable that the side flap fixing part 32 is installed on the extended line of the leg gathers 27 and that the first joint part 35 and the second joint part 36 are installed at the outer end part 37 in the width direction of the diaper body 12.

For the above top sheet 18, used are materials which are liquid hydrophilic and are not irritative to the skin. Such materials include non-woven fabric itself or a combination with other materials, the non-woven fabric being obtained by a manufacturing method such as melt blown, spun bonding, point bonding, through air, needle punch, wet spun lace, and so on. Also fibrous sheets include a sheet being formed from those fibers of which ingredients are rayon, acetate, cotton pulp, or synthetic resin, or a combination thereof so as to make a core-sheath structure.

The aforementioned back sheet 20 may be composed of what is capable of preventing leakage of excrement absorbed in the absorbent body 22. Also, by employing a material having moisture permeability, moisture in wearing can be reduced and discomfort in wearing can be reduced. As such materials, it is possible to use, for example, a sheet film where synthetic resin is made into a film, aerated film obtained by filling inorganic filler and applying drawing treatment, laminates combining paper, non-woven fabric and film, aerated liquid block sheet having openings 10 to 30% with pore diameters ranging from 0.1 to 0.6 mm obtained by positioning capillaries toward the side of the absorbent body, and the like. Also, preferable is thermal processing film embossed to create a fabric-like appearance.

It is preferable that the above absorbent bodies 22 are those having a function to absorb and retain excrement such as urine and that the absorbent bodies are bulky, unlikely to lose shape, and chemically less irritative. Generally, it is possible to use pulp, chemical pulp, rayon, acetate, natural cotton, super absorbent polymer, super absorbent polymer fiber, synthetic fibers, or a combination thereof. A shape and structure of the absorbent body 22 can be changed if necessary, however it is necessary to make a total absorbed quantity of the absorbent body 22 correspond to a designed absorption quantity as the disposable diaper and the desired use. A size absorbing ability of the absorbent 22 can be changed depending on wearers from children to adults.

Materials used for the above side flap 14 may be non-woven fabric having elasticity or not having elasticity.

The non woven fabric having elasticity is composed of at least one layer of an elastic sheet and one layer of non-woven fabric. Its composition is carried out by laminate, heat, sonic, mechanical junction, and the like. The elastomer used for the elastic sheet comprises a sheet being composed of high molecular weight polymer such as polyurethane, styrene-butadiene-styrene block copolymer (SBS), styrene-butadiene-ethylene-styrene block copolymer (SBES), styrene-isoprene-styrene block copolymer (SIS); a net being formed with the above-mentioned high molecular weight polymer, or a fiber-like elastic member formed with the above-mentioned high molecular weight polymer. This elastic sheet and the non-woven fabric can be joined through entanglement by sonication, hot melt, needle punch, high pressure fluid treatment, and the like in addition to the method to join and integrate by heating/pressure bonding.

The elastic sheet comprises a fiber aggregate which is elastically capable of expanding and contracting at least in one direction and is composed of fibers with diameters from 0.1 to 50 μm, more preferably from 0.5 to 30 μm, and is composed of long fibers being formed from thermoplastic elastic polymer such as styrene elastomer and urethane. The aggregate of these fibers may include a plurality of continuous fibers formed by continuously extruding by the direct fiber spinning method such as spun bond and melt blown. Also, it is possible to use thermally bonded non-woven fabric made of elastic yarns and films made of thermoplastic elastic polymers.

On the other hand, the non-elastic non-woven fabrics comprises non-woven fabrics such as spun bond, point bond, through air bondg, chemical bond, melt brown, spun lace and needle punch. As fibers thereof, it is possible to use sheath-core type composite fibers and side-by-side type composite fibers made of polyolefin, polyester, polyamide, or polyethylene/polypropylene or polyethylene/polyester. A typical example of this non-woven fabric is an aggregate of elasticizable continuous fibers, which is non-elastically capable of expanding in the direction where the elastic sheet expands. This continuous fiber has a fiber diameter of 0.1 to 50 μm, more preferably 5 to 30 μm, and formed of polyethylene, polypropylene, ethylene/propylene copolymer, ethylene/propylene/butene copolymer, or mixtures thereof, or composite fibers thereof. A specific weight per unit of the non-woven fabric is 2 to 100 g/cm$^2$, more preferably 7 to 20 g/cm$^2$. The aggregate can be obtained by irregularly depositing a plurality of the continuous fibers continuously extruded by the general direct spinning method such as the melt brown or spun bond method on a belt conveyor running in one direction.

For a reference, the elastic side flap used as an example of the present invention is composed of three layers, has a configuration where a film having elasticity and a specific weight per unit from 100 to 200 g/cm$^2$ is sandwiched between two non-woven fabrics having a specific weight per unit from 5 to 50 g/cm$^2$, and is embossed and joined by sonic bonding. This elastic side flap has a stress property where the elasticity is from 900 to 1900 mN when stretched at 75%, from 500 to 1500 mN when stretched at 50%, and from 100 to 1000 mN when stretched at 30%, in back stress of the second cycle when stretched at 100%.

The above fastener is fixedly attached around the waist part so that the disposable diaper 10 does not slip off when the disposable diaper is worn, and has a configuration where a hook tape (male engaging piece) is partially affixed on a fastening tape substrate 16a made of an elongated rectangular non-woven fabric. One end part of a back side of the fastening tape substrate where the hook tape is affixed is joined and fixed to the outer end part 37 of the side flap 14. The joining and fixing is carried out by laminate, heating, sonication, mechanical joint, or the like as described in the joint of the non-woven fabric mentioned above. A fastener may be used such that the non-woven fabric (e.g., specific weight per unit of 80 g/cm$^2$) by spun bond or point bond is employed as the fastening tape substrate, the specific weight per unit being 80 g/cm$^2$, and a surface fastener (male engaging piece) is attached on one surface of this substrate.

Figure 3:
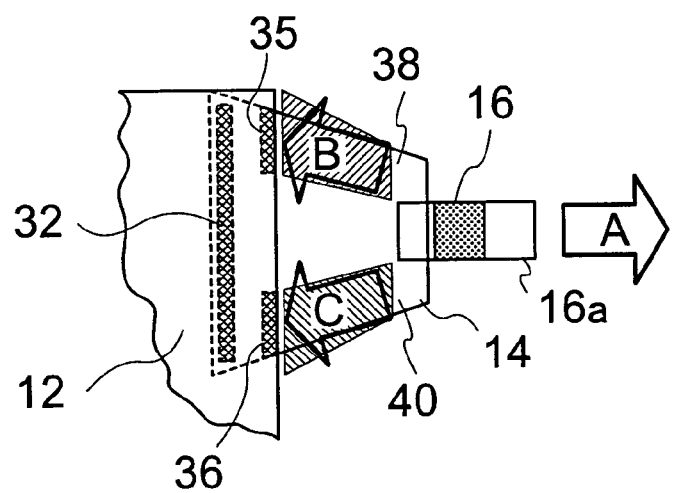
FIG. 3 is an enlarged partial front view showing distribution of tensile force when a fastener of the disposable diaper is pulled according to the first embodiment of the present invention.
Figure 4:
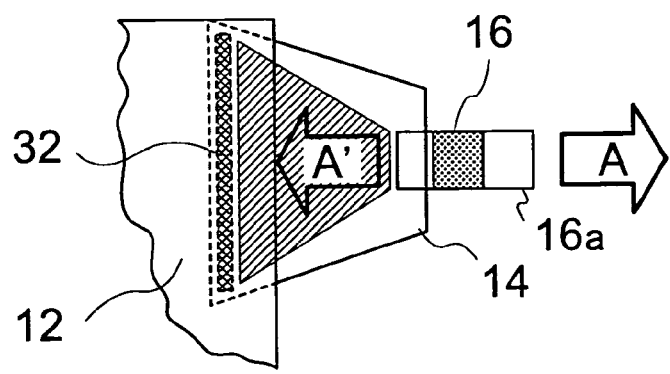
FIG. 4 is an enlarged partial front view showing distribution of tensile force when a fastener of the disposable diaper is pulled according to the first embodiment of the present invention where a side flap and a diaper body are fixed only at a side flap fixing part.

Next, the distribution of tensile force when the fastener is pulled is described referring to FIGS. 3 and 4.

FIG. 3 is a figure showing the distribution of the tensile force when the fastener 16 is pulled for the disposable diaper according to the present invention. FIG. 3 is a figure showing the distribution of the tensile force when the fastener is pulled for the disposable diaper where the side flap 14 and the diaper body 12 are fixed only at the side flap fixing part 32 (hereinafter, referred to as disposable diaper in a conventional configuration).

When the disposable diaper 10 is worn, the fastener in a state where the tensile force "A" is applied by a wearer is fixed to the diaper body 12 so as to fit to a body of the wearer.

In the disposable diaper of the first embodiment of the present invention, the side flap 14 is fixed to the diaper body 12 at the side flap fixing part 32, and additionally is joined to the diaper body 12 at two sites of the first joint part 35 and the second joint part 36. These joint parts are joined to the diaper body 12 at the side outer than the side flap fixing part 32, in the width direction of the diaper body 12. In this configuration, as shown in FIG. 3, the tensile force "A" applied to the fastener 16 is divided into a force "B" distributed to the side edge upper area 38 of the side flap and a force "C" distributed to the side edge lower area 40 of the side flap, which thereafter act on the first joint part 35 and the second joint part 36, respectively.

In this manner, the tensile force "A" applied to the fastener 16 is effectively and directly concentrated to the side edge upper area 38 of the side flap and the side edge lower area 40 of the side flap, i.e., around the waist and legs of the wearer of the disposable diaper.

This improves fitness around the waist and legs, and enables to fill in gaps between openings of the disposable diaper and the body and makes leakage of excrement difficult.

On the other hand, in the case of the disposable diaper having the conventional configuration, as shown in FIG. 4, the tensile force "A" applied to the fastener is interlocked with the diaper body 12 as "A'", and covers around the waist of the wearer completely and evenly. This is inferior in fitness around the legs and there is a possibility of causing leakage of excrement.

The disposable diaper here is a disposable diaper having a diaper body with a top sheet, back sheet, and absorbent body enclosed between said top sheet and said back sheet, and a pair of side flaps fixed to said diaper body at the side flap fixing part and the joint parts, wherein said diaper body has a pair of parallel side end parts in the longitudinal direction of said diaper body, each of said side end part has the first end part and the second end part located at the opposite side of said first end part, said side flap fixing part and the joint parts are located at said first end part of said disposable diaper, said side flap fixing part is located at the side inner than said joint parts on the basis of the width direction of said diaper body, said each side flap has an inner end part which is the inner side on the basis of the width direction of said diaper body and the outer end part which is the outer side on the basis of the width direction of said diaper body, and the fastener is fixed at each outer end part of said side flap.

In this configuration, the tensile force "A" applied to the fastener is divided into the force "B" distributed from the side edge upper area 38 of the side flap and the force "C" distributed from the side edge lower area 40 of the side flap, therefore the tensile force applied to the fastener is exerted by effectively being divided into the waist area and the leg areas of the wearer of the disposable diaper.

This enables to improve fitness around the waist and legs, respectively, and enables to fill in gaps between openings of the disposable diaper and the body and makes leakage of excrement difficult.

Figure 5:
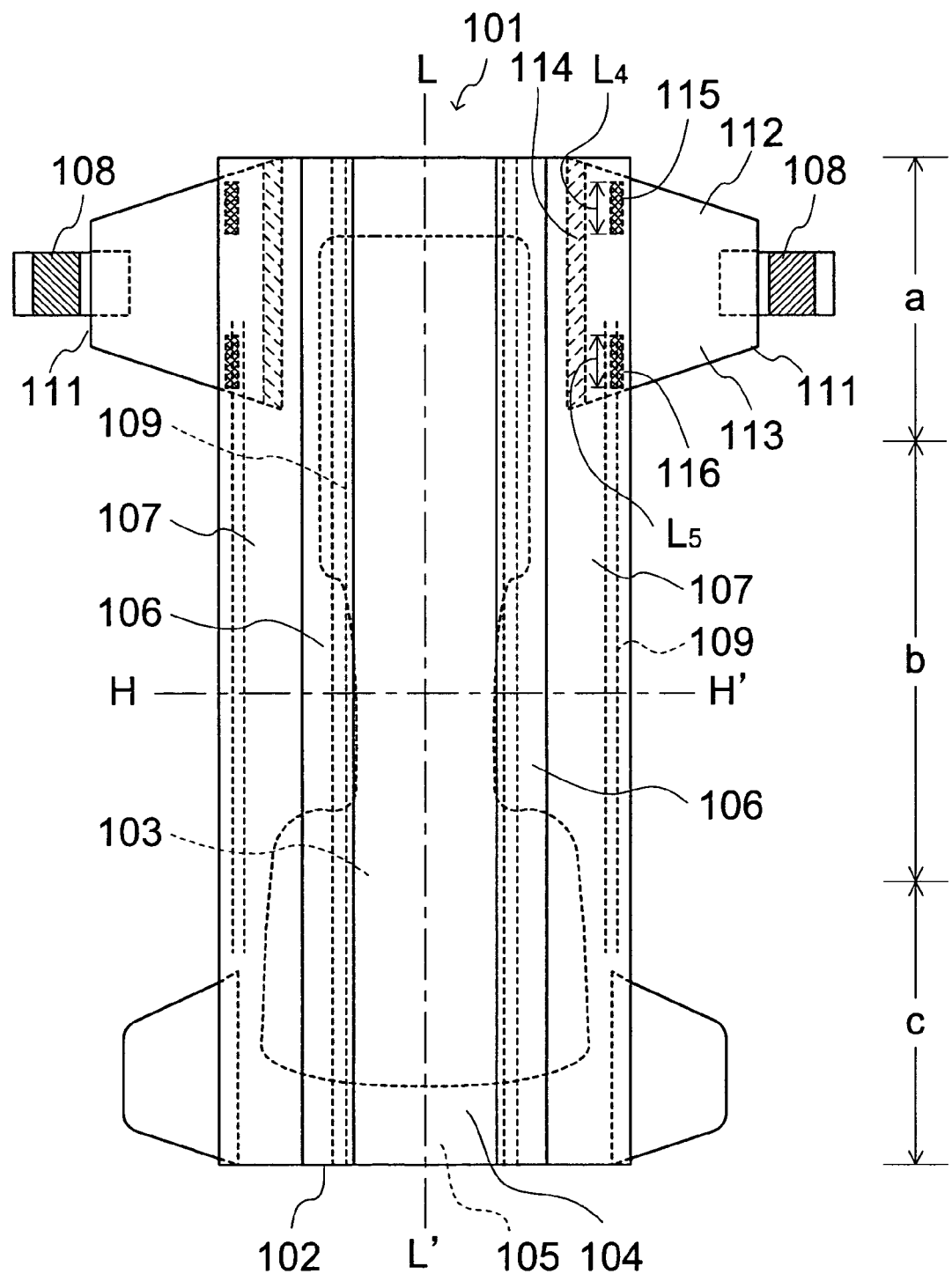
FIG. 5 is a developed view of the second embodiment according to the present invention where a body side face (face in contact with the skin of a wearer) is directed toward an observer.
Figure 6:
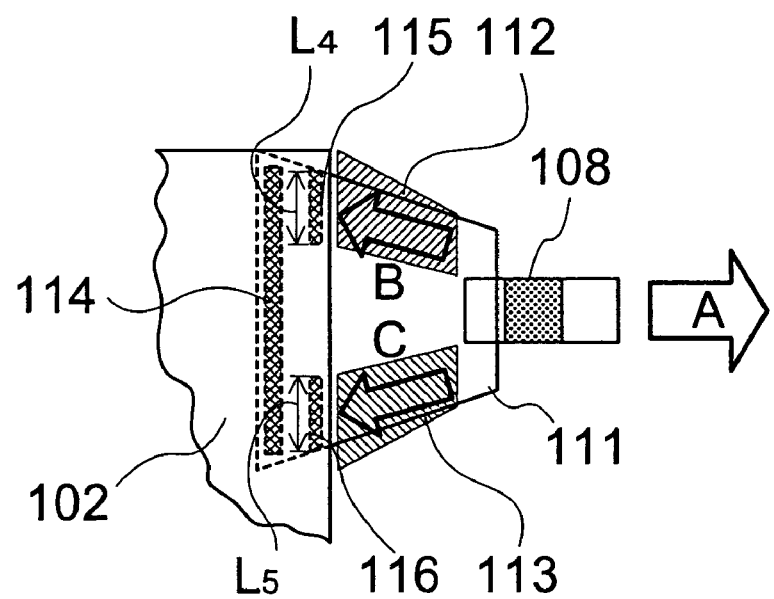
FIG. 6 is an enlarged partial front view showing distribution of tensile force when the fastener of the disposable diaper is pulled according to the second embodiment of the present invention.
Figure 7:
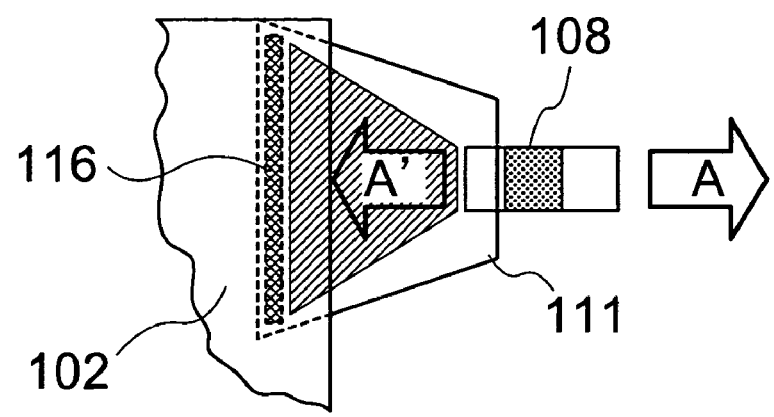
FIG. 7 is an enlarged partial front view showing distribution of tensile force when fastening means of the conventional disposable diaper is pulled where side flaps and a diaper body are fixed only at a fixing part.

FIG. 5 is a developed view of the disposable diaper according to the second embodiment of the present invention. In the developed view, the body side surface or the face contacting with skin of wearer, is directed toward an observer. FIG. 6 is an enlarged partial front view showing distribution of tensile force when the fastener of the disposable diaper is pulled according to the second embodiment of the present invention. FIG. 7 is an enlarged partial front view showing distribution of tensile force when fastening means of the conventional disposable diaper is pulled where side flaps and a diaper body are fixed only at a fixing part.

As shown in FIG. 5, the disposable diaper of the present invention has a first waist area "a", a groin area "b", and a second waist area "c". FIG. 2 shows a sectional view of the disposable diaper along H-H' line in FIG. 1. The disposable diaper includes a diaper body 102, a pair of side flaps 114 extending in the width direction of the diaper body 12 (the H-H' direction in the drawing) in the vicinity of a longitudinal direction end part at the first waist area "a", and a pair of fastening means 108 installed on a side end of each side flap 111.

The diaper body 102 has a substantially rectangular shape and comprises a liquid permeable top sheet 104 which comes into contact with the skin of a wearer, a liquid impermeable back sheet 105 which is provided on the garment side, an absorbent body 103 having an hourglass shape, steric gathers 106 installed on a top sheet 104 face at both sides of this absorbent body 103, elastic members 109 positioned along the longitudinal direction (L-L' direction in the drawing) of the diaper body 102, which impart elasticity to the steric gathers 106. The top sheet 104 and the back sheet 105 have greater length and width than the absorbent body 103 and extend beyond the outside of the absorbent body 103. The diaper body 102 has leg gathers 107 at least in the groin part area "b". Elastic members 109 are positioned to impart elasticity to these leg gathers 107.

Also, the side flap 111 is not a member continuous with the diaper body 102, and is arranged as another member at a dorsal side of the diaper body 12. Alternatively, the side flap 111 may be arranged at a ventral side.

The side flap 111 is fixed to the diaper body 102 at a side flap fixing part 114. Further, the side flap 111 is joined to the diaper body 12 at two sites, a first joint part 115 located at an upper part of the side end 112 and a second joint part 116 located at a lower part of the side end 113. The first joint part 115 and the second joint part 116 are installed apart in the longitudinal direction (L-L' direction) of the disposable diaper 101. The first joint part 115 and the second joint part 116 are joined to the diaper body 102 in the positions which are in the outer side in the width direction of the diaper body compared with the side flap fixing part 114. Further, the length $L_4$ of the first joint part 115 is substantially the same as the length $L_5$ of the second joint part 115.

The side flap fixing part 114, the first joint part 115 and the second joint part 116, which join the side flap 114 and the diaper body 102, are joined between the top sheet 104 and the back sheet 105 by a thermal method such as heating/pressure bonding with heat seal, sonic seal, hot melt adhesive, or the like. In this embodiment, the side flap 111 is placed between the top sheet 104 and the back sheet 105. However, the side flap 111 may be arranged in a surface of the back sheet, which corresponds to the garment side or opposite side of the body. Alternatively, the side flap 111 may be arranged in a surface of the top sheet, which corresponds to the body side. In this case, edge parts of the side flap 111 would contact with the body, the consideration should be taken to soften the edge part.

The side flap fixing part 111 is placed such that an inner side of the side flap 111 is located on an extended line of the leg gathers 107 or at an inner site in the width direction than the extended line of the leg gathers 107. On the other hand, the first joint part 115 and the second joint part 116 are placed at an outer site in the width direction of the diaper body 102 and at an outer site than an extended line of the leg gathers 27 in the width direction of the diaper body 12, apart from the side flap fixing part 114. It is preferable that the side flap fixing part 114 is installed on the extended line of the leg gathers 107 and that the first joint part 35 and the second joint part 36 are installed at the side end in the longitudinal direction of the diaper body 12.

Hereinafter, behavior of the tensile forces when fastening means 108 of the disposable diaper 101 is pulled according to the second embodiment of the present invention.

FIG. 6 is an enlarged partial front view showing distribution of tensile force when the fastener of the disposable diaper is pulled according to the second embodiment of the present invention. FIG. 7 is an enlarged partial front view showing distribution of tensile force when fastening means of the conventional disposable diaper is pulled where side flaps and a diaper body are fixed only at a fixing part.

Upon wearing the disposable diaper 101, fastening means 108 is fixed to the diaper body 102 while pulling force "A" is applied by a wearer, thereby the diaper body being fitted.

As shown in FIGS. 5 and 6, in the disposable diaper 101, the side flap 111 is fixed to the diaper body 102 at the side flap fixing part 114, and further joined to the diaper body 102 at two sites, the first joint part 115 and the second joint part 116 of the side flap 111. The joint parts are joined to the diaper body 102 at the outer side more than the side flap fixing part 114 in the width direction of the diaper body 102 and where the length $L_4$ of the first joint part 115 is the same as the length $L_5$ of the second joint part 116. In this configuration, as shown in FIG. 6, the tensile force A applied to the fastener means 108 is divided into the force B interlocking with the side edge upper end area 112 and the force C interlocking with the side edge lower end area 113, which thereafter act on the first joint part 115 and the second joint part 116, respectively, in a manner where the force C interlocking with the side edge lower end area 113 is about the same as the force B interlocking with side edge upper end area 112.

Therefore, the tensile force A given to the fastener means 108 is divided into about the same forces in side edge upper end area 112 and the side edge lower end area 113 so that about the same force is applied to areas around the legs and areas around the waist effectively and intensively.

This enables to improve fitness around the waist and legs, respectively, and enables to fill in gaps between openings of the disposable diaper and the body and makes leakage of excrement difficult.

On the other hand, in the case of the disposable diaper having the conventional configuration, as shown in FIG. 7, the tensile force "A" applied to the fastener is interlocked with the diaper body 12 as force "A'", and covers around the waist of the wearer completely and evenly. This is inferior in fitness around the legs and there is a possibility of causing leakage of excrement.

Third Embodiment

Figure 8:
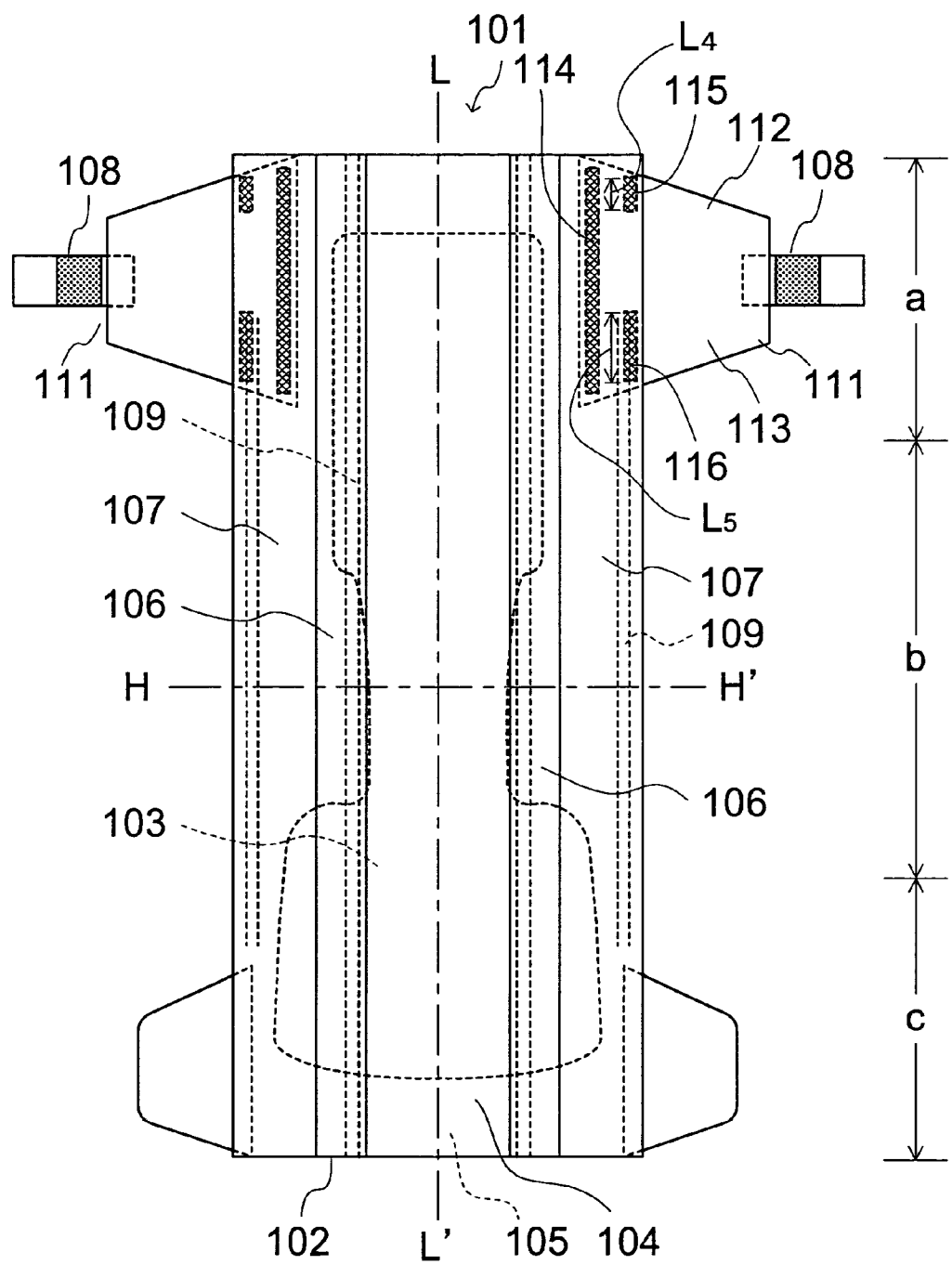
FIG. 8 is a developed view of the third embodiment according to the present invention where a body side face (face in contact with the skin of a wearer) is directed toward an observer.
Figure 9:
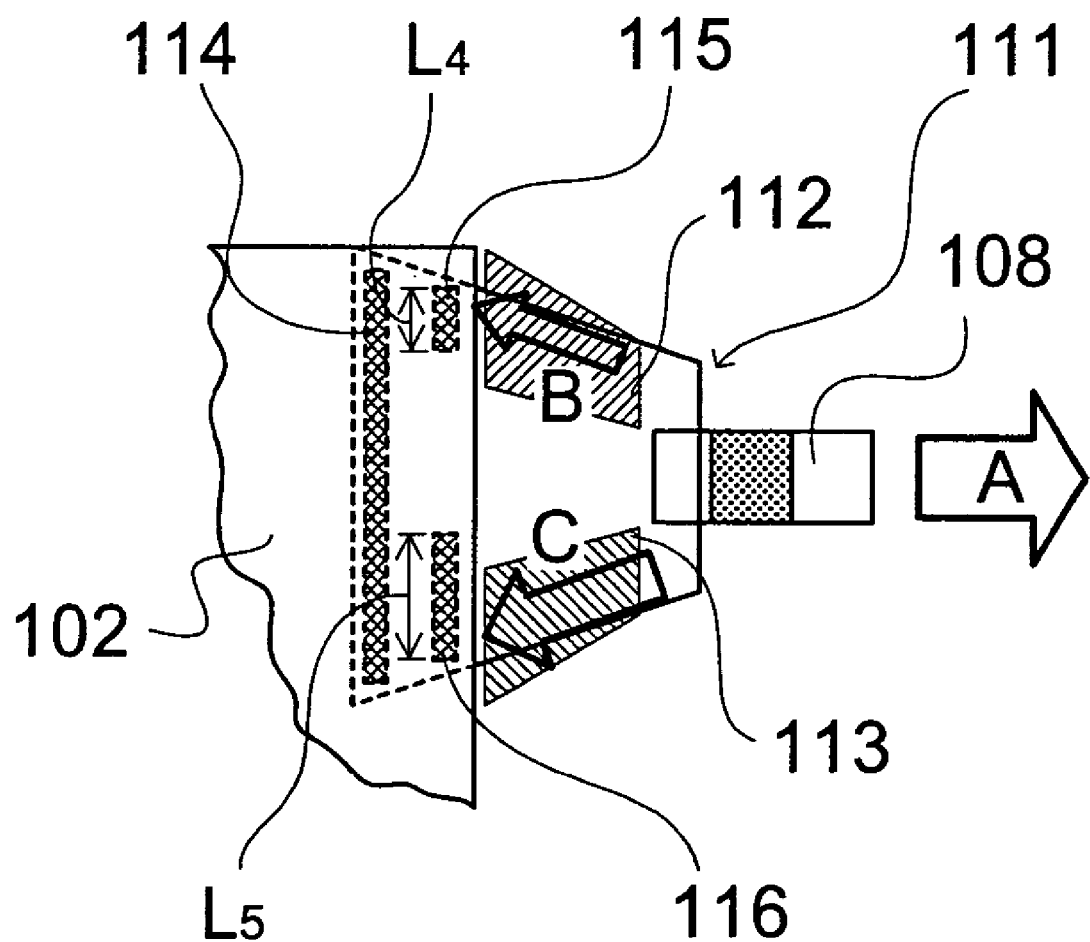
FIG. 9 is an enlarged partial front view showing distribution of the tensile force when the fastener of the disposable diaper is pulled according to the third embodiment of the present invention.

FIG. 8 is a developed view of the third embodiment according to the present invention, a figure where a body side face (face in contact with the skin of a wearer) is directed toward an observer, and FIG. 9 is a figure showing the behavior of the tensile force when a fastener means is pulled for a disposable diaper in the third embodiment. In the following embodiments, identical symbols are given to the same elements as those in the second embodiment, and overlapping descriptions thereof are omitted.

In this third embodiment, for a first joint part 115 and a second joint part 116 of a side flap 111 positioned along a longitudinal direction end part of a diaper body 102 in the second embodiment mentioned above, lengths of the joint parts 115 and 116 are different. That is, as shown in FIG. 8, the length $L_4$ of the first joint part 115 is shorter than the length $L_5$ of the second joint part 116.

This disposable diaper 101 has a first waist area "a", a groin area "b" and a second waist area "c" as in the second embodiment. And, the diaper is made up of the diaper body 102, a pair of side flaps 111 extending in the width direction (a horizontal direction centerline H-H' direction in the figure) of the diaper body 102 in the vicinity of the longitudinal direction end part at the first waist area "a" and a pair of fastener means 108 placed at a side edge of each side flap 111.

The diaper body 102 is made up of a liquid permeable top sheet 104 which comes into contact with the skin of a wearer, a liquid impermeable back sheet 105 which becomes the garment side, an absorbent 103 enclosed by these sheets with the whole shape being approximately rectangular and hourglass-formed, steric gathers 106 installed at four faces of the top sheet at nearly both side parts of this absorbent 103, and elastic members 109 which are installed along the longitudinal direction (direction of vertical direction centerline L-L' in the figure) of these steric gathers 106 and impart elasticity to the steric gathers 106. The top sheet 104 and the back sheet 105 are larger than the absorbent 103 in length and width and extend beyond edges of the absorbent 103 to the outsides, at least the leg gathers 107 are formed at the groin area "b", and the elastic members 109 are positioned to impart elasticity to these leg gathers 107.

Also, the side flaps 111 are positioned at the ventral side (first waist area "a") of the diaper body 102 as separated members not as members contiguous with the diaper body 102. These may be positioned at the dorsal side (second waist area "c").

And, this side flap 111 is fixed to the diaper body 102 at a side flap fixing part 114. Further, the side flap 111 is joined to the diaper body 102 at two sites, a side edge upper end area 112 and a side edge lower end area 113 to form the first joint part 115 and the second joint part 116, respectively. The first joint part 115 and the second joint part 116 of this side flap 111 are installed apart in the longitudinal direction (a vertical direction centerline L-L' direction) of the diaper 1, and are joined to the diaper body 102 in the width direction of the diaper body 102 and at an outer side more than the side flap fixing part 114. Also, different from the second embodiment, the lengths of the first joint part 115 and the second joint part 116 of the side flap 111 are formed at a dimension where the length $L_4$ of the first joint part 115 of the side flap 111 is shorter than the length $L_5$ of the second joint part 116.

Additionally, this side flap 111 is positioned to be sandwiched between the top sheet 104 and the back sheet 105, but may be positioned at a surface (garment side at an opposite body face to the body side face) of the back sheet 105 of the diaper body 102. Also, a method for joining the side flap 111 and the diaper body 102, a position of the side flap fixing part 114 and materials used for the members which comprise the disposable diaper 101 are the same as those in the second embodiment, and thus are omitted.

Next, behavior of the tensile force when the fastener means 108 is pulled for the disposable diaper 101 in this third embodiment is described based on FIG. 9.

As shown in FIGS. 8 and 9, in the disposable diaper 101 of the present invention, the side flap 111 is fixed to the diaper body 102 at the side flap fixing part 114, and further joined to the diaper body 102 at two sites, the first joint part 115 and the second joint part 116 of the side flap 111. The joint parts are joined to the diaper body 102 in the width direction of the diaper body 102 and at the outer side more than the side flap fixing part 114 at a dimension where the length $L_4$ of the first joint part 115 is shorter than the length $L_5$ of the second joint part 116. In this configuration, as shown in FIG. 9, the tensile force A applied to the fastener means 108 is divided into the force B interlocking with the side edge upper end area 112 and the force C interlocking with the side edge lower end area 113, which thereafter act on the first joint part 115 and the second joint part 116, respectively, in a manner where the force C interlocking with the side edge lower end area 113 is larger than the force B interlocking with side edge upper end area 112.

Therefore, the tensile force A given to the fastener means 108 imparts actions so that areas around the legs are more effectively and intensively pulled than areas around the waist, thus resulting in a better fitness at areas around the legs of the wearer.

Fourth Embodiment

Figure 10:
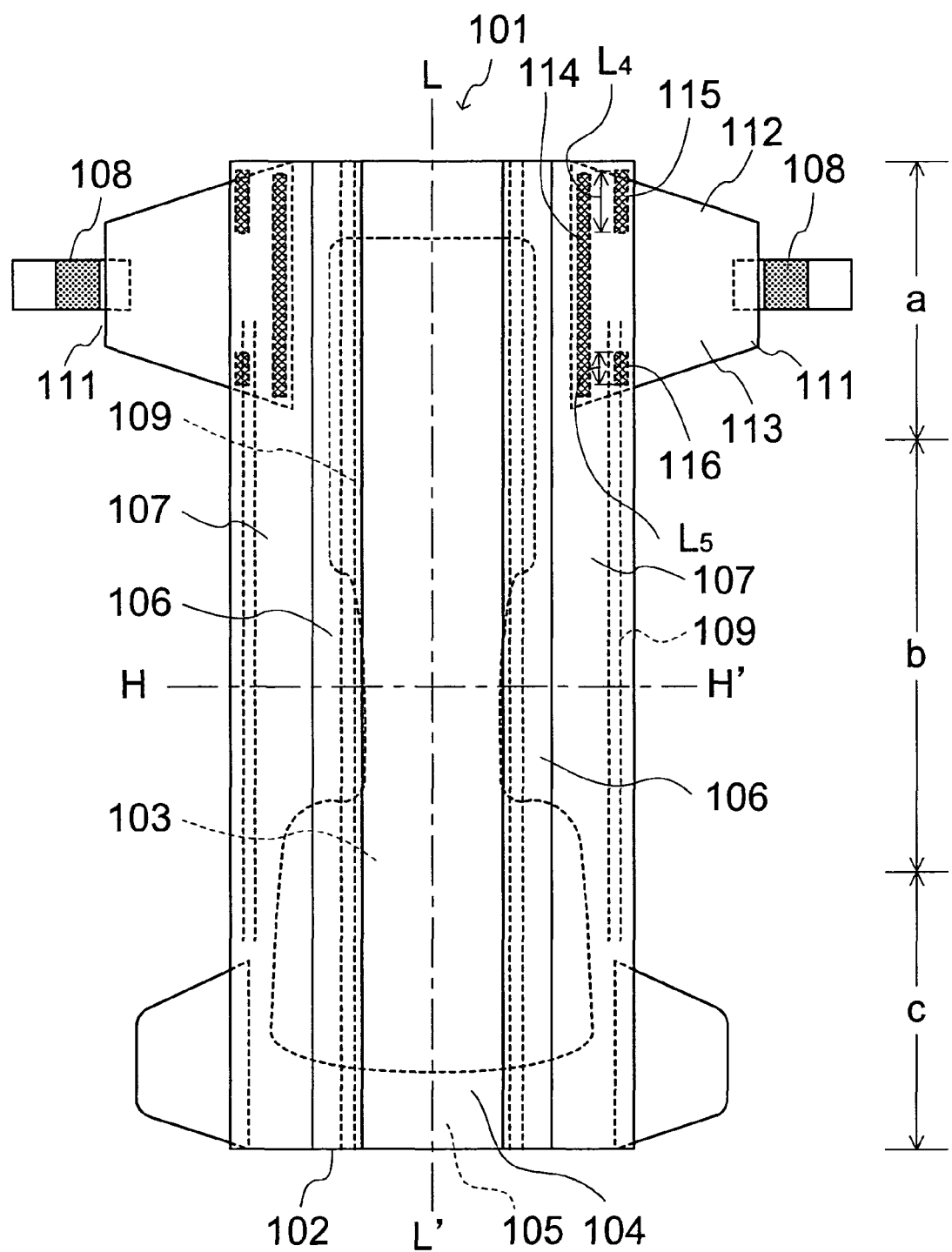
FIG. 10 is a developed view of the fourth embodiment according to the present invention where a body side face (face in contact with the skin of a wearer) is directed toward an observer.
Figure 11:
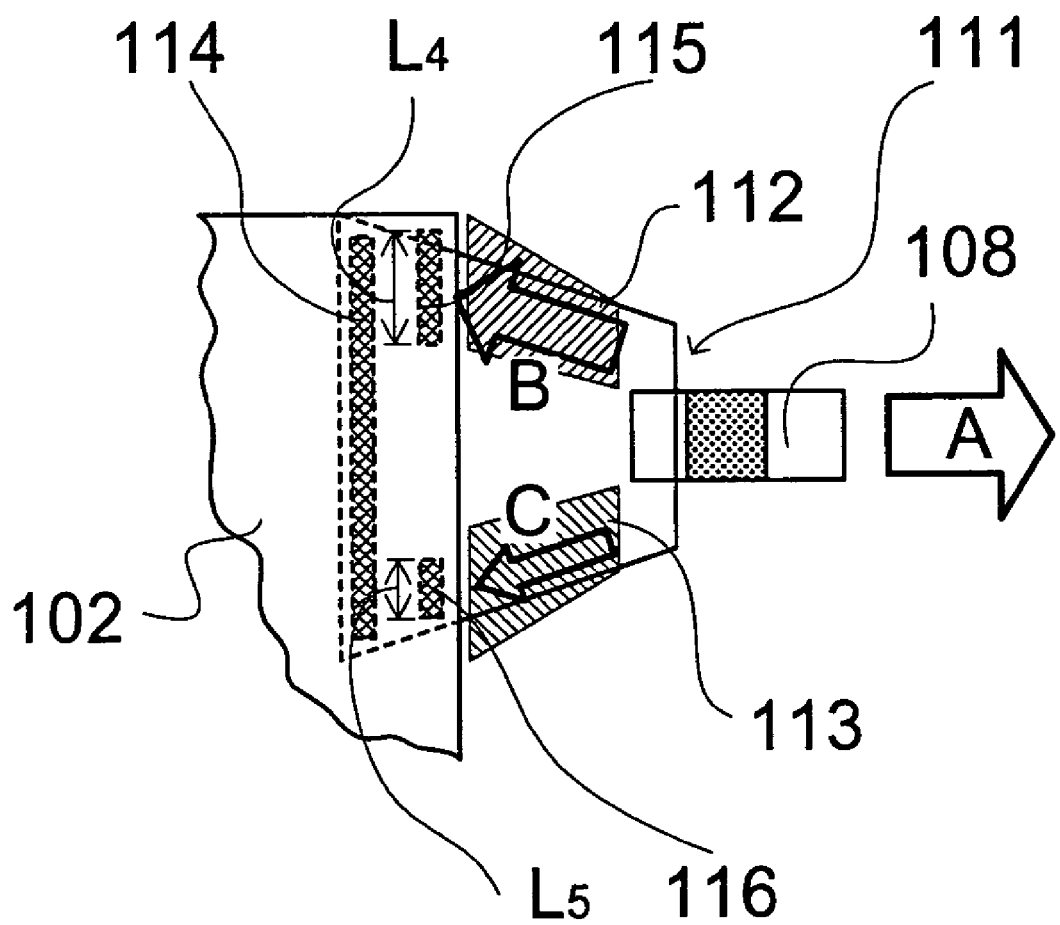
FIG. 11 is an enlarged partial front view showing distribution of the tensile force when the fastener of the disposable diaper is pulled according to the fourth embodiment of the present invention.

FIG. 10 is a developed view of the fourth embodiment according to the present invention, a figure where the body side face (face in contact with the skin of a wearer) is directed toward the observer, and FIG. 11 is a figure showing the behavior of the tensile force when the fastener means is pulled for the disposable diaper of the fourth embodiment. In the following embodiments, identical symbols are given to the same elements as those in the second embodiment, and overlapping descriptions thereof are omitted.

In the fourth embodiment, lengths different for the joint parts 115 and 116 of the side flap 111 positioned along the longitudinal direction end part of the diaper body 102 is reversed in the third embodiment mentioned above. That is, as shown in FIG. 10, the length $L_4$ of the first joint part 115 is longer than the length $L_5$ of the second joint part 116.

This disposable diaper 101 has the first waist area "a", the groin area "b" and the second waist area "c" as in the second embodiment. And, the diaper is made up of the diaper body 102, a pair of side flaps 111 extending in the width direction (the horizontal direction centerline H-H' direction in the figure) of the diaper body 102 in the vicinity of the longitudinal direction end part at the first waist area "a" and a pair of fastener means 108 installed at the side edge of each side flap 111.

The diaper body 102 is made up of the liquid permeable top sheet 104 which comes into contact with the skin of a wearer, the liquid impermeable back sheet 105 which becomes the garment side, the absorbent 103 enclosed by these sheets with a whole shape being approximately rectangular and hourglass-formed, steric gathers 106 installed at four faces of the top sheet at nearly both side parts of this absorbent 103, and elastic members 109 which are installed along the longitudinal direction (a vertical direction centerline L-L' direction in the figure) of these steric gathers 106 and impart elasticity to the steric gathers 106. The top sheet 104 and the back sheet 105 are larger than the absorbent 103 in length and width and extend beyond edges of the absorbent 103 to the outsides, at least the leg gathers 107 are formed at the groin area "b", and the elastic members 109 are positioned to impart elasticity to these leg gathers 107.

Also, the side flaps 111 are positioned at the ventral side (first waist area "a") of the diaper body 102 as separated members not as members contiguous with the diaper body 102. These may be positioned at the dorsal side (second waist area "c").

And, this side flap 111 is fixed to the diaper body 102 at the side flap fixing part 114. Further, the side flap 111 is joined to the diaper body 102 at two sites, the side edge upper end area 112 and the side edge lower end area 113 to form the first joint part 115 and the second joint part 116, respectively. The first joint part 115 and the second joint part 116 of this side flap 111 are installed apart in the longitudinal direction (the vertical direction centerline L-L' direction) of the disposable diaper 101, and are joined to the diaper body 102 in the width direction of the diaper body 102 and at the outer side more than the side flap fixing part 114. Also, different from the first and third embodiments, the lengths of the first joint part 115 and the second joint part 116 of the side flap 111 are formed at a dimension where the length $L_4$ of the first joint part 115 of the side flap 111 is longer than the length $L_5$ of the second joint part 116.

Additionally, this side flap 111 is positioned to be sandwiched between the top sheet 104 and the back sheet 105, but may be positioned at the surface (garment side at the opposite body face to the body side face) of the back sheet 105 of the diaper body 102. Also, the method for joining the side flap 111 and the diaper body 102, the position of the side flap fixing part 114 and materials used for the members which comprise the disposable diaper 101 are the same as those in the second embodiment, and thus are omitted.

Next, the behavior of the tensile force when the fastener means 108 is pulled for the disposable diaper 101 in this fourth embodiment is described based on FIG. 11.

As shown in FIGS. 6 and 7, in the disposable diaper 101 of the present invention, the side flap 111 is fixed to the diaper body 102 at the side flap fixing part 114, and further joined to the diaper body 102 at two sites, the first joint part 115 and the second joint part 116 of the side flap 111. The joint parts are joined to the diaper body 102 in the width direction of the diaper body 102 and at the outer side more than the side flap fixing part 114 at a dimension where the length $L_4$ of the first joint part 115 is longer than the length $L_5$ of the second joint part 116. In this configuration, as shown in FIG. 11, the tensile force A applied to the fastener means 108 is divided into the force B interlocking with the side edge upper end area 112 and the force C interlocking with the side edge lower end area 113, which thereafter act on the first joint part 115 and the second joint part 116, respectively, in the manner where the force B interlocking with the side edge upper end area 112 of the side flap 111 is larger than the force C interlocking with side edge lower end area 113 of the side flap 111.

Therefore, the tensile force A given to the fastener means 108 imparts actions so that areas around the legs are more effectively and intensively pulled than areas around the waist, thus resulting in a better fitness at areas around the legs of the wearer.

Fifth Embodiment

Figure 12:
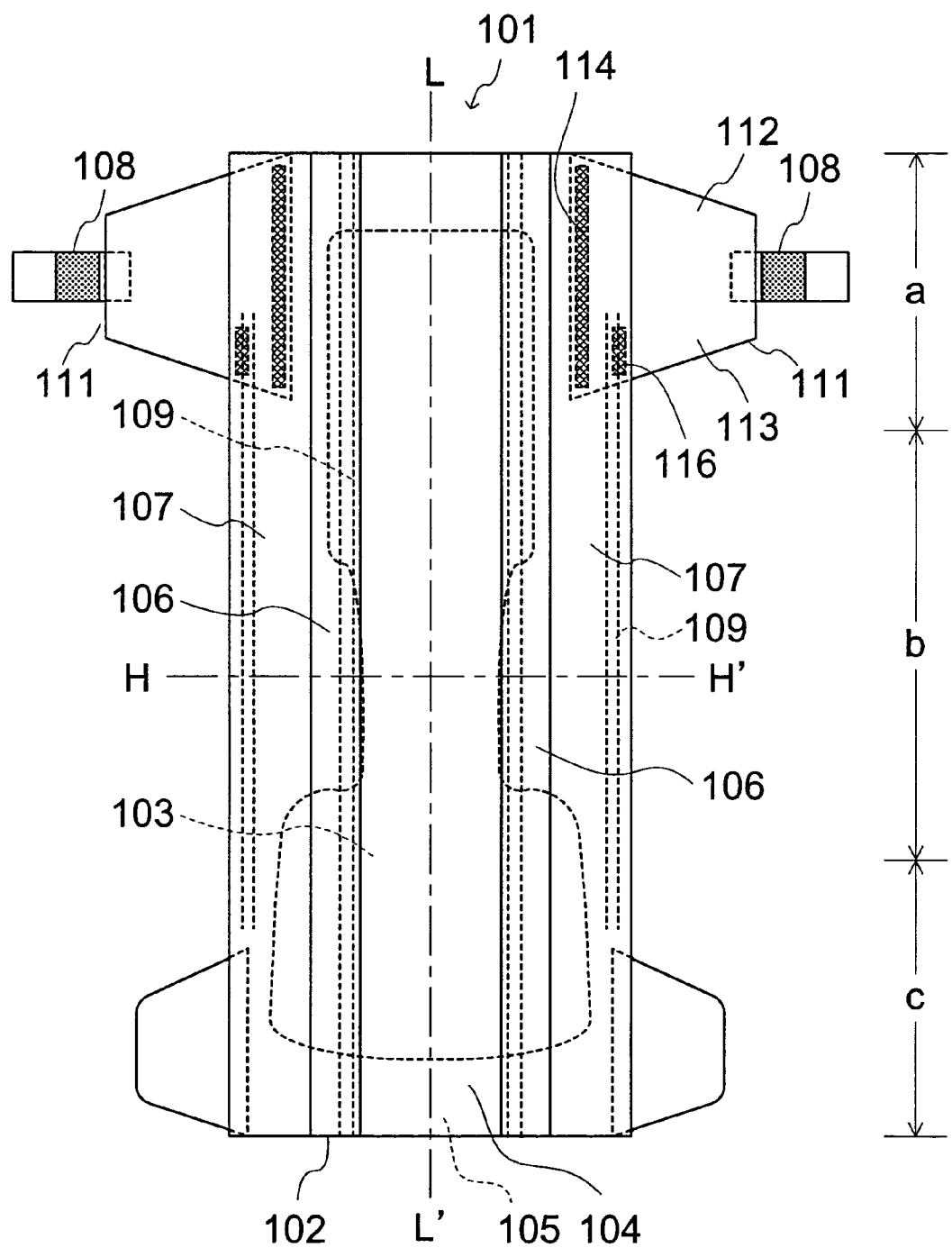
FIG. 12 is a developed view of the fifth embodiment according to the present invention where a body side face (face in contact with the skin of a wearer) is directed toward an observer.
Figure 13:
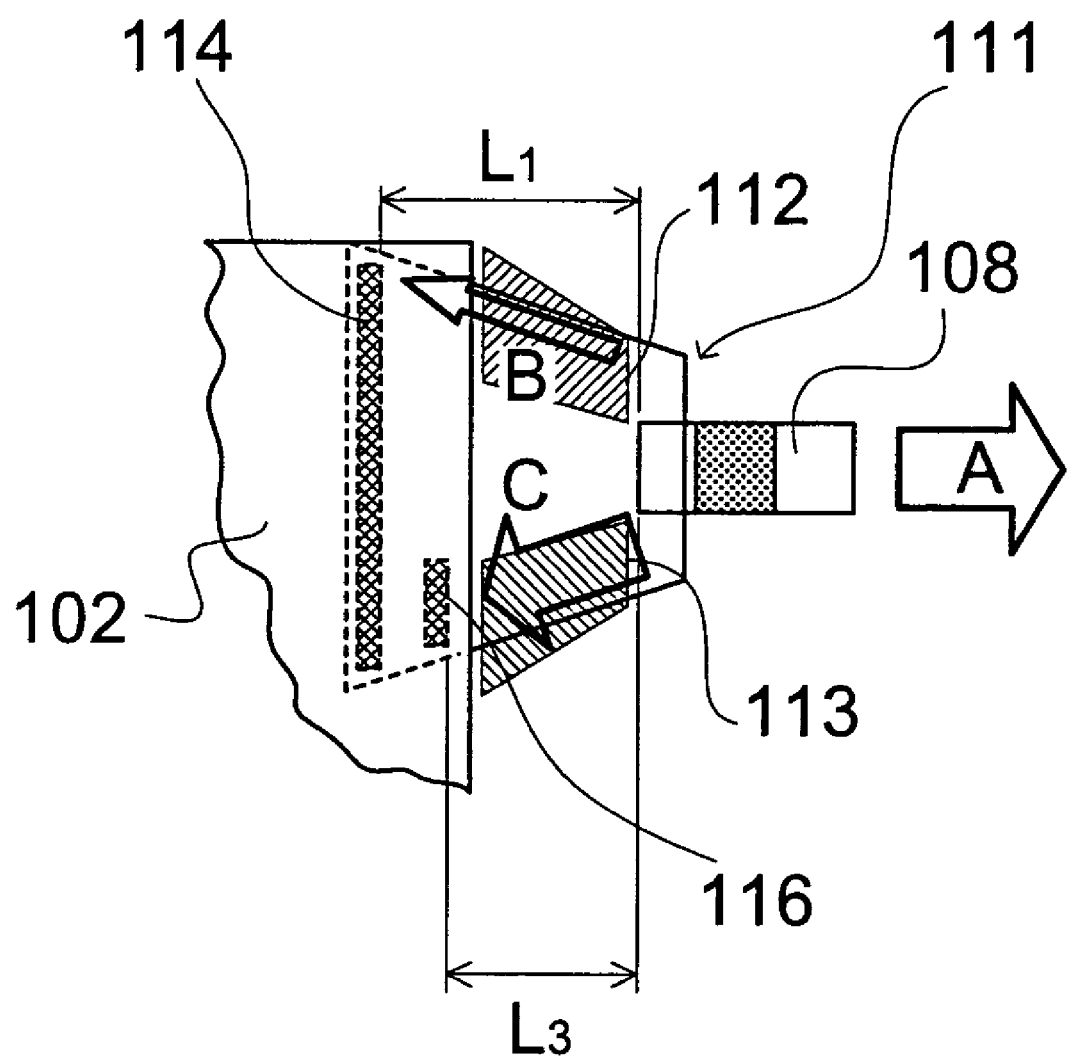
FIG. 13 is an enlarged partial front view showing distribution of the tensile force when the fastener of the disposable diaper is pulled according to the fifth embodiment of the present invention.

FIG. 12 is a developed view of the fifth embodiment according to the present invention, a figure where the body side face (face in contact with the skin of a wearer) is directed toward the observer, and FIG. 13 is a figure showing the behavior of the tensile force when the fastener means is pulled for the disposable diaper in the fifth embodiment. In the following embodiments, identical symbols are given to the same elements as those in the second embodiment, and overlapping descriptions thereof are omitted.

In this fifth embodiment, only the second joint part 116 is made in the first joint part 115 and the second joint part 116 of the side flap 111 positioned along the longitudinal direction end part of the diaper body 102 as in the second embodiment mentioned above. That is, as shown in FIG. 12, no joint part (the first joint part 115) is present at the side edge upper end part 12 of the side flap 111, and the second joint part 116 is placed at the side edge lower end part 13 of the side flap 111.

This disposable diaper 101 has the first waist area "a", the groin area "b" and the second waist area "c" as in the second embodiment. And, the diaper is made up of the diaper body 102, a pair of side flaps 111 extending in the width direction (the horizontal direction centerline H-H' direction in the figure) of the diaper body 102 in the vicinity of the longitudinal direction end part at the first waist area "a" and a pair of fastener means 108 placed at the side edge of each side flap 111.

The diaper body 102 is made up of the liquid permeable top sheet 104 which comes into contact with the skin of a wearer, the liquid impermeable back sheet 105 which becomes the garment side, the absorbent 103 enclosed by these sheets with the whole shape being approximately rectangular and hourglass-formed, the steric gathers 106 installed at four faces of the top sheet at nearly both side parts of this absorbent 103, and the elastic members 109 which are installed along the longitudinal direction (the vertical direction centerline L-L' direction in the figure) of these steric gathers 106 and impart elasticity to the steric gathers 106. The top sheet 104 and the back sheet 105 are larger than the absorbent 103 in length and width and extend beyond edges of the absorbent 103 to the outsides, at least the leg gathers 107 are formed at the groin area "b", and the elastic members 109 are positioned to impart elasticity to these leg gathers 107.

Also, the side flaps 111 are positioned at the ventral side (first waist area "a") of the diaper body 102 as separated members not as members contiguous with the diaper body 102. These may be positioned at the dorsal side (second waist area "c").

And, this side flap 111 is fixed to the diaper body 102 at the side flap fixing part 114. Further, the side flap 111 is joined to the diaper body 102 at the side edge lower end area 113 to form the second joint part 116 of the side flap 111. The second joint part 116 of this side flap 111 is located at the side edge of the diaper body 102 in the width direction (the horizontal direction centerline H-H' direction in the figure) of the diaper body 102 and at the outer side more than the side flap fixing part 114.

Additionally, this side flap 111 is positioned to be sandwiched between the top sheet 104 and the back sheet 105, but may be positioned at the surface (garment side at the opposite body face to the body side face) of the back sheet 105 of the diaper body 102. Also, the method for joining the side flap 111 and the diaper body 102, the position of the side flap fixing part 114 and materials used for the members which comprise the disposable diaper 101 are the same as those in the second embodiment, and thus are omitted.

Next, the behavior of the tensile force when the fastener means 108 is pulled for the disposable diaper 101 in this fifth embodiment is described based on FIG. 13.

In the disposable diaper 101 of the present invention, as shown in FIGS. 8 and 9, the side flap 111 is fixed to the diaper body 102 at the side flap fixing part 114, further joined to the diaper body 102 at the second joint part 116 of the side flap 111, and this second joint part 116 is located at the side edge of the diaper body 102 in the width direction (the horizontal direction centerline H-H' direction in the figure) of the diaper body 102 and at the outer side more than the side flap fixing part 114. Thus, as shown in FIG. 13, an interval dimension $L_3$ between the second joint part 116 of the side flap 111 and the fastener means 108 (hereinafter referred to as an effective length between the second joint part 116 of the side flap 111 and the fastener means 108) is shorter than the interval dimension $L_1$ between the side flap fixing part 114 and the fastener means 108 (hereinafter referred to as the effective length between the side flap fixing part 114 and the fastener means 108). In this configuration, as shown in FIG. 13, the tensile force A applied to the fastener means 108 is divided into the force B interlocking with the side edge upper end area 112 and the force C interlocking with the side edge lower end area 113, which thereafter act on an upper area of each side flap fixing part 114 and the second joint part 116 of the side flap 111, respectively, in the manner where the force B interlocking with the side edge upper end area 112 of the side flap 111 is smaller than the force C interlocking with the side edge lower end area 113.

Therefore, the tensile force A given to the fastener means 108 imparts actions so that areas around the legs are more effectively and intensively pulled than areas around the waist, thus resulting in a better fitness at areas around the legs of the wearer.

Sixth Embodiment

Figure 14:
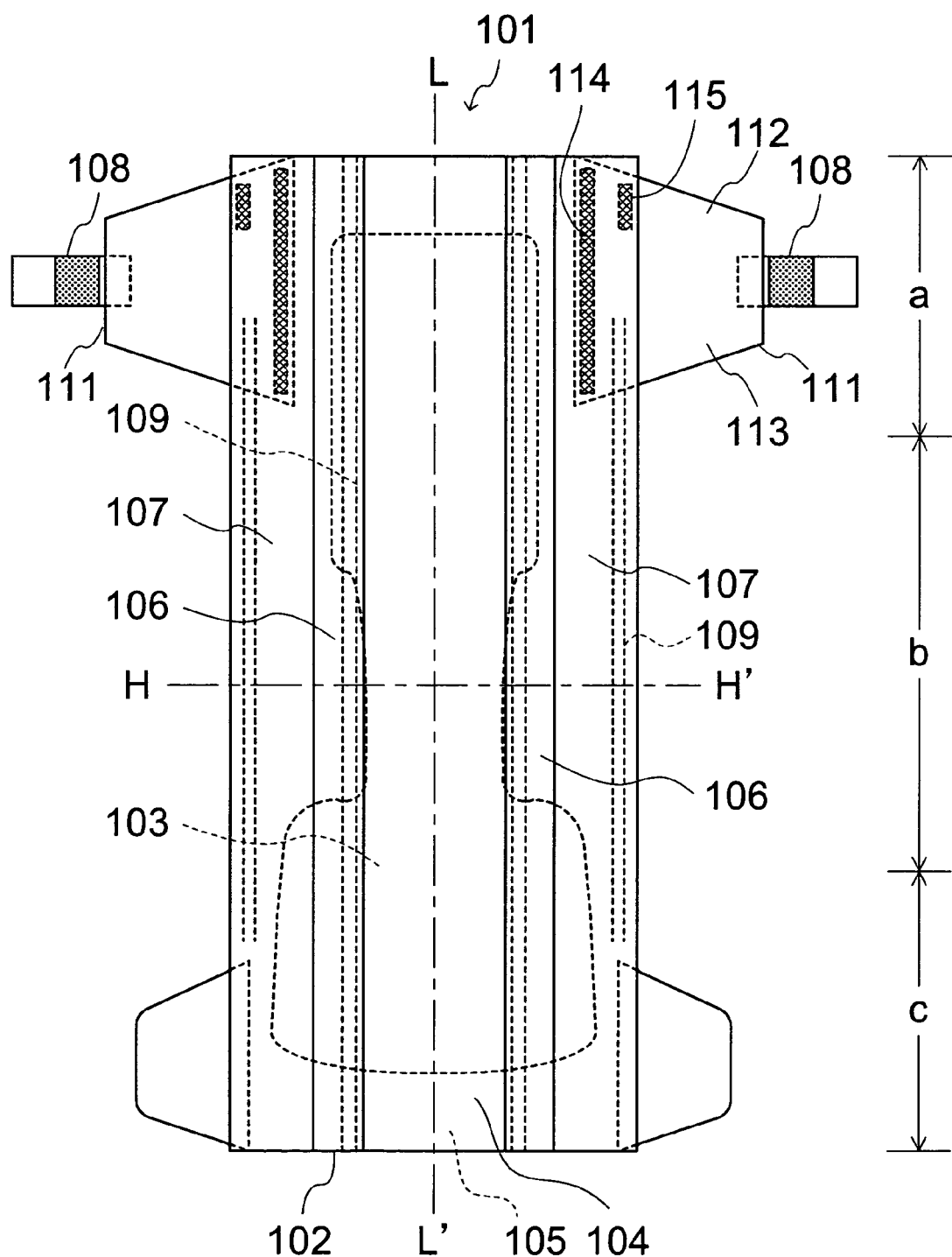
FIG. 14 is a developed view of the sixth embodiment according to the present invention where a body side face (face in contact with the skin of a wearer) is directed toward an observer.
Figure 15:
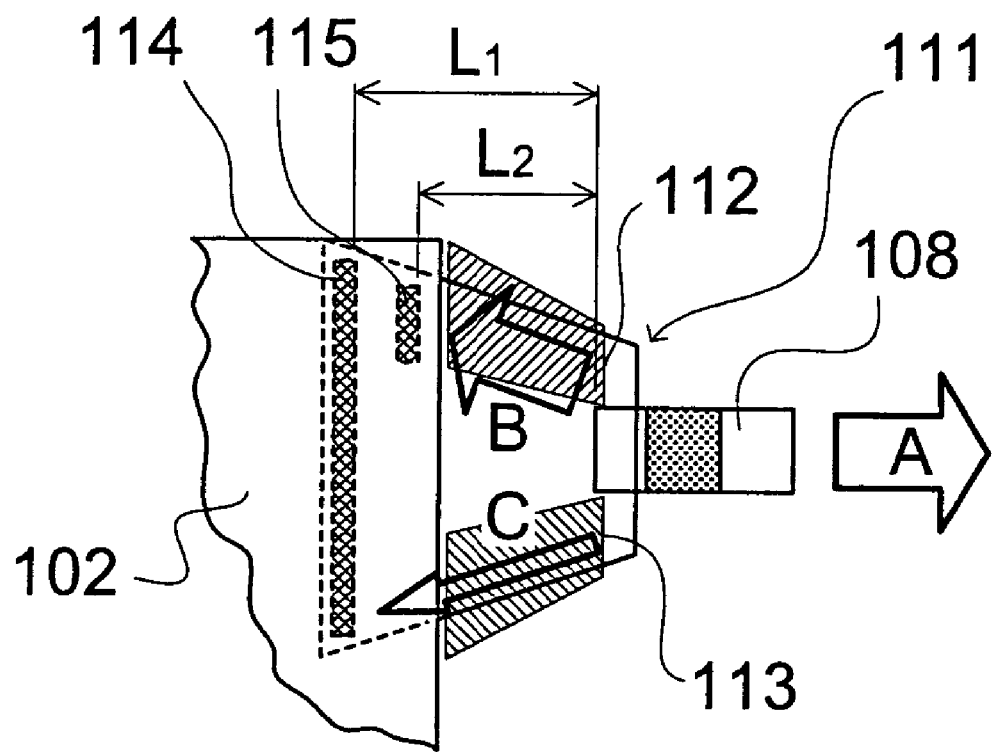
FIG. 15 is an enlarged partial front view showing distribution of the tensile force when the fastener of the disposable diaper is pulled according to the sixth embodiment of the present invention.

FIG. 14 is a developed view of the sixth embodiment according to the present invention, a figure where the body side face (face in contact with the skin of a wearer) is directed toward the observer, and FIG. 15 is a figure showing the behavior of the tensile force when the fastener means is pulled for the disposable diaper in the sixth embodiment. In the following embodiments, identical symbols are given to the same elements as those in the second embodiment, and overlapping descriptions thereof are omitted.

In this sixth embodiment, the first joint part 115 is placed at the side edge upper end area 112 in place of the second joint part 116 placed at the side edge lower end area 113 of the side flap 111 positioned along the longitudinal direction end part of the diaper body 102. That is, as shown in FIG. 14, no joint part (second joint part 116) is present at the side edge lower end area 113 of the side flap 111, and the first joint part 115 is placed at the side edge upper end area 112 of the side flap 111.

This disposable diaper 101 has the first waist area "a", the groin area "b" and the second waist area "c" as in the second embodiment. And, the diaper is made up of the diaper body 102, a pair of side flaps 111 extending in the width direction (the horizontal direction centerline H-H' direction in the figure) of the diaper body 102 in the vicinity of the longitudinal direction end part at the first waist area "a" and a pair of fastener means 108 placed at the side edge of each side flap 111.

The diaper body 102 is made up of the liquid permeable top sheet 104 which comes into contact with the skin of a wearer, the liquid impermeable back sheet 105 which becomes a garment side, the absorbent 103 enclosed by these sheets with the whole shape being approximately rectangular and hourglass-formed, the steric gathers 106 installed at four faces of the top sheet at nearly both side parts of this absorbent 103, and the elastic members 109 which are installed along the longitudinal direction (a vertical direction centerline L-L' direction in the figure) of these steric gathers 106 and impart elasticity to the steric gathers 106. The top sheet 104 and the back sheet 105 are larger than the absorbent 103 in length and width and extend beyond edges of the absorbent 103 to the outsides, at least the leg gathers 107 are formed at the groin area "b", and the elastic members 109 are positioned to impart elasticity to these leg gathers 107.

Also, the side flaps 111 are positioned at the ventral side (first waist area "a") of the diaper body 102 as separated members not as members contiguous with the diaper body 102. These may be positioned at the dorsal side (second waist area "c").

And, the side flap 111 is fixed to the diaper body 102 at the side flap fixing part 114, and the side flap 111 is joined to the diaper body 102 at the side edge upper end area 112 to form the first joint part 115. The first joint part 115 of the side flap 111 is located at the side edge of the diaper body 102 in the width direction (horizontal direction centerline H-H' direction) of the diaper body 102.

Additionally, this side flap 111 is positioned at the surface (garment side at an opposite body face to the body side face) of the back sheet 105 of the diaper body 102 as in the second embodiment, but may be positioned to be sandwiched between the top sheet 104 and the back sheet 105. Also, the method for joining the side flap 111 and the diaper body 102, the position of the side flap fixing part 114 and materials used for the members which comprise the disposable diaper 101 are the same as those in the second embodiment, and thus are omitted.

Next, the behavior of the tensile force when the fastener means 108 is pulled for the disposable diaper 101 in this sixth embodiment is described based on FIG. 15.

In the disposable diaper 101 of the present invention, as shown in FIGS. 10 and 11, the side flap 111 is fixed to the diaper body 102 at the side flap fixing part 114, and the side flap 111 is joined to the diaper body 102 at the side edge upper end area 112 to form the first joint part 115. The first joint part 115 of this side flap 111 is located at the side edge of the diaper body 102 in the width direction (vertical direction centerline H-H' direction in the figure) of the diaper body 102 and at the outer side more than the side flap fixing part 114. Thus, as shown in FIG. 15, the effective length $L_2$ between the first joint part 115 of the side flap 111 and the fastener means 108 is shorter than the effective length $L_1$ between the side flap fixing part 114 and the fastener means 108. In this configuration, the tensile force A applied to the fastener means 108 is divided into the force B interlocking with the side edge upper end area 112 and the force C interlocking with the side edge lower end area 113, which thereafter act on the first joint part 115 and a lower area of the side flap fixing part 114, respectively, in the manner where the force B interlocking with the side edge upper end area 112 of the side flap 111 is larger than the force C interlocking with the side edge lower end area 113.

Therefore, the tensile force A given to the fastener means 108 imparts actions so that areas around the legs are more effectively and intensively pulled than areas around the waist, thus resulting in a better fitness at areas around the legs of the wearer.

Seventh Embodiment

Figure 16:
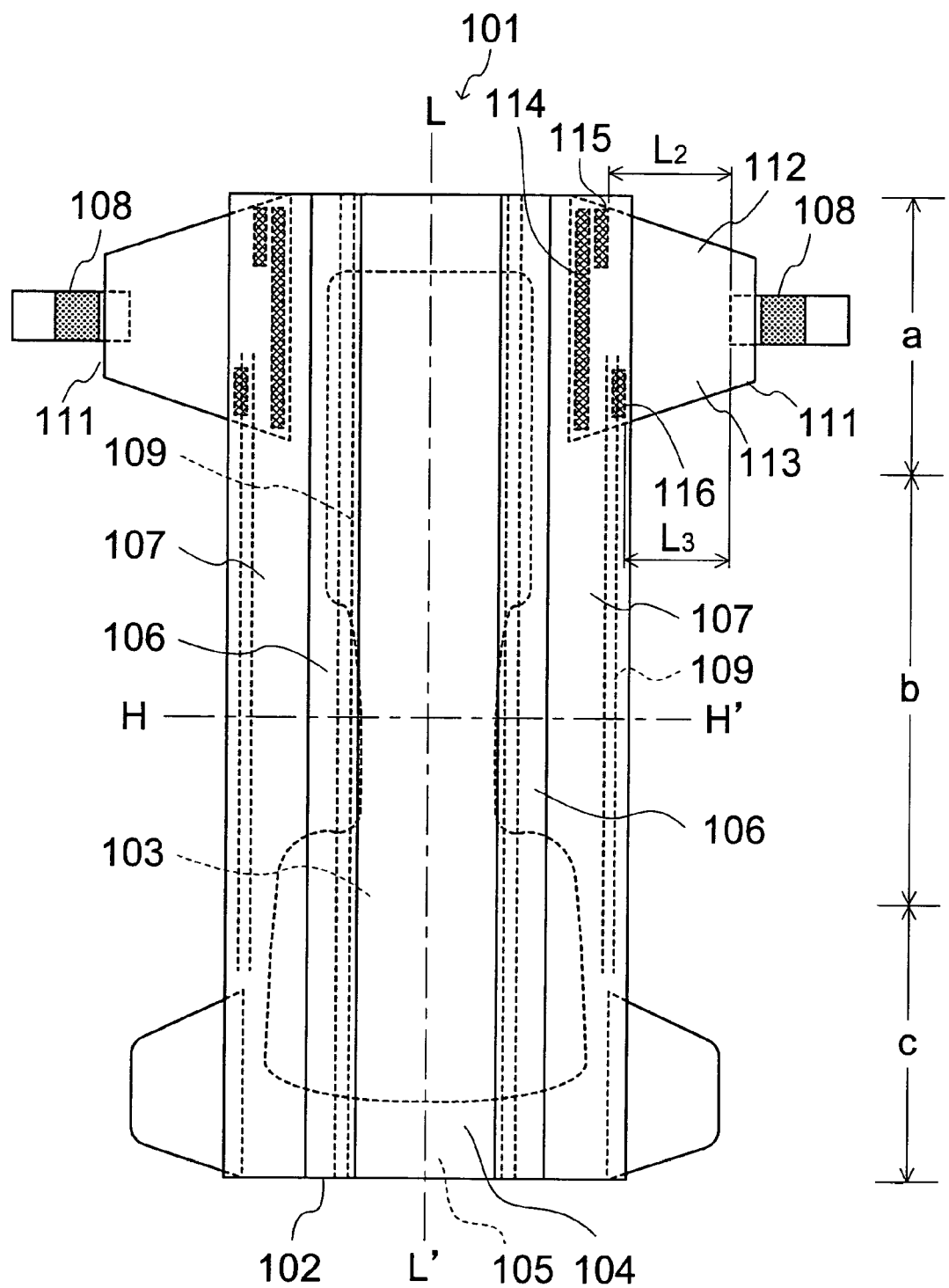
FIG. 16 is a developed view of the seventh embodiment according to the present invention where a body side face (face in contact with the skin of a wearer) is directed toward an observer.
Figure 17:
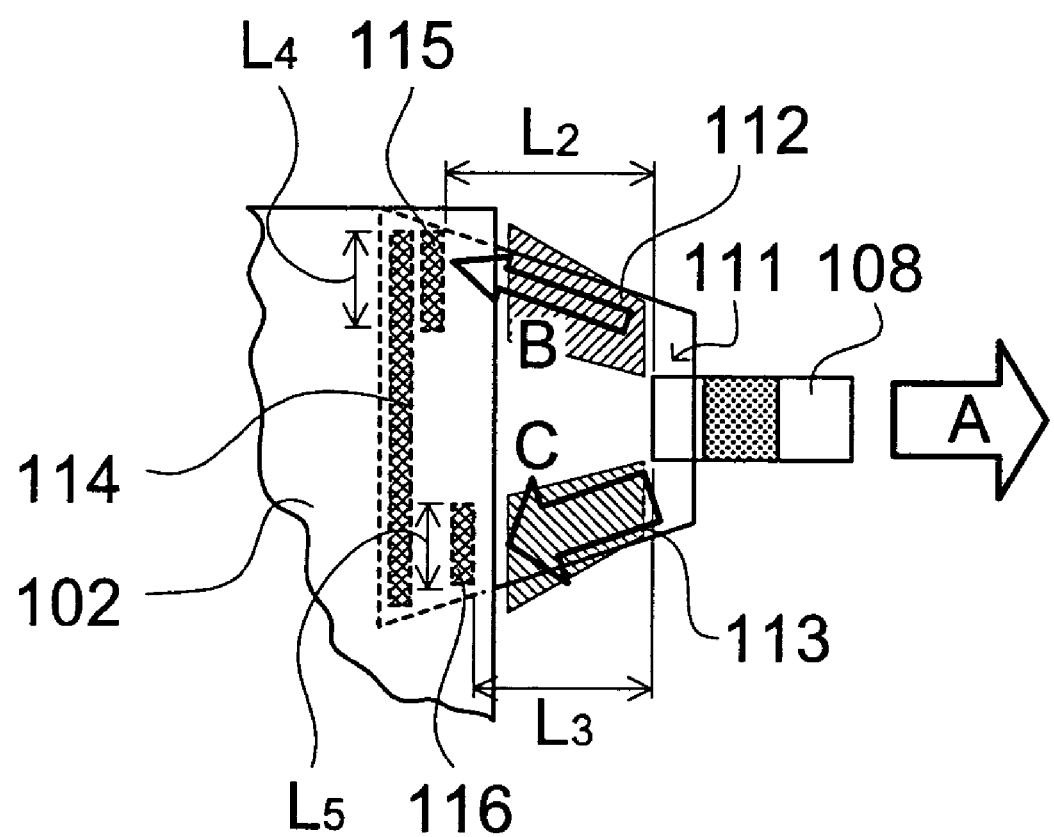
FIG. 17 is an enlarged partial front view showing distribution of the tensile force when the fastener of the disposable diaper is pulled according to the seventh embodiment of the present invention.

FIG. 16 is a developed view of the seventh embodiment according to the present invention, a figure where a body side face (face in contact with the skin of a wearer) is directed toward an observer, and FIG. 17 is a figure showing the behavior of the tensile force when a fastener means is pulled for a disposable diaper in the seventh embodiment. In the following embodiments, identical symbols are given to the same elements as those in the second embodiment, and overlapping descriptions thereof are omitted.

The seventh embodiment is similar to the foregoing second embodiment but different in the locations at which the joint parts 115 and 116 of the side flap 111 installed along the longitudinal end parts of the diaper body 102 are provided. More particularly, as illustrated in FIG. 16, the first joint part 115 of the side flap 111 is provided outside the side flap fixing part 114 and in the vicinity of the side flap fixing part 114, and the second joint part 116 is provided outside the width direction of the diaper body 102 (direction of horizontal centerline H-H') and at the side edge of the diaper body 102.

As in the second embodiment, this disposable diaper 101 is also provided with the first waist area "a" and groin area "b" as well as the second waist area "c", and composed of diaper body 102, a pair of side flaps 111 extending in the width direction of the diaper body 102 (direction of horizontal centerline H-H' in the figure) at the first waist area "a" and in the vicinity of the longitudinal end part and a pair of fasteners 8 installed at the side edges of the respective side flaps 111.

The diaper body 102 is made up of a liquid permeable top sheet 104 which comes into contact with the skin of a wearer, a liquid impermeable back sheet 105 which becomes the garment side, an absorbent 103 enclosed by these sheets with the whole shape being approximately rectangular and hourglass-formed, steric gathers 106 installed at four faces of the top sheet at nearly both side parts of this absorbent 103, and elastic members 109 which are installed along the longitudinal direction (direction of vertical direction centerline L-L' in the figure) of these steric gathers 106 and impart elasticity to the steric gathers 106. The top sheet 104 and the back sheet 105 are larger than the absorbent 103 in length and width and extend beyond edges of the absorbent 103 to the outsides, at least the leg gathers 107 are formed at the groin area "b", and the elastic members 109 are positioned to impart elasticity to these leg gathers 107.

Also, the side flaps 111 are positioned at the ventral side (first waist area "a") of the diaper body 102 as separated members not as members contiguous with the diaper body 102. These may be positioned at the dorsal side (second waist area "c").

The side flap 111 is fixed with the diaper body 102 at the side flap fixing part 114. Further, the side flap 111 is joined to the diaper body 102 at two sites, namely, at the side edge upper end area 112 and the side edge lower end area 113, respectively forming the first joint part 115 and the second joint part 116. The first joint part 115 and the second joint part 116 of the side flap 111 are similar in length, provided apart from each other in the longitudinal direction of the disposable diaper 101 (direction of longitudinal center line L-L'), and at the same time, the first joint part 115 of the side flap 111 is located outside the side flap fixing part 114 and in the vicinity of the side flap fixing part 114, and the second joint part 116 of the side flap 111 is located in the width direction of the diaper body 102 (direction of horizontal centerline H-H') and at the side edge of the diaper body 102. More particularly, a configuration is given so that the effective length $L_2$ between the first joint part 115 of the side flap 111 and the fastener means 108 is longer than the effective length $L_3$ between the second joint part 116 of the side flap 111 and the fastener means 108.

The side flap 111 is installed so as to be sandwiched between the top sheet 104 and the back sheet 105, and may be installed on the surface of the back sheet 105 of the diaper body 102 (opposite to the body and on the side of a garment). Further, the method for joining the side flap 111 with the diaper body 102 and the location of the side flap fixing part 114 and materials used for the members forming the disposable diaper 101 are the same as those given in the second embodiment, and overlapping descriptions are omitted.

Next, behavior of the tensile force when the fastener means 108 is pulled for the disposable diaper 101 in this seventh embodiment is described based on FIG. 17.

As illustrated in FIG. 16 and FIG. 17, in the disposable diaper 101 of the present invention, the side flap 111 is fixed with the diaper body 102 at the side flap fixing part 114, and the side flap 111 is also joined with the diaper body 102 at two sites, namely, at the side edge upper end area 112 and the side edge lower end area 113, respectively forming the first joint part 115 and the second joint part 116. The first joint part 115 and the second joint part 116 of the side flap 111 are provided apart from each other in the longitudinal direction of the disposable diaper 101 (direction of longitudinal center line L-L'), and at the same time the first joint part 115 of the side flap 111 is located outside the side flap fixing part 114 and in the vicinity of the side flap fixing part 114, and the second joint part 116 of the side flap 111 is located outside the width direction of the diaper body 102 (direction of horizontal centerline H-H') and at the side edge of the diaper body 102. More particularly, as FIG. 17, a configuration is given so that the effective length $L_2$ between the first joint part 115 of the side flap 111 and the fastener means 108 is longer than the effective length $L_3$ between the second joint part 116 of the side flap 111 and the fastener means 108. In this configuration, as illustrated in FIG. 17, the tensile force A given to the fastener means 108 is divided into force B interlocking with the side edge upper end area 112 and force C interlocking with the side edge lower end area 113 in such a fashion that the force B interlocking with the side edge upper end area 112 of the side flap 111 is smaller than the force C interlocking with the side edge lower end area 113 of the side flap 111, thus respectively acting on the first joint part 115 and the second joint part 116.

Therefore, the tensile force A given to the fastener means 108 imparts actions so that areas around the legs are more effectively and intensively pulled than areas around the waist, thus resulting in a better fitness at areas around the legs of the wearer.

Eighth Embodiment

Figure 18:
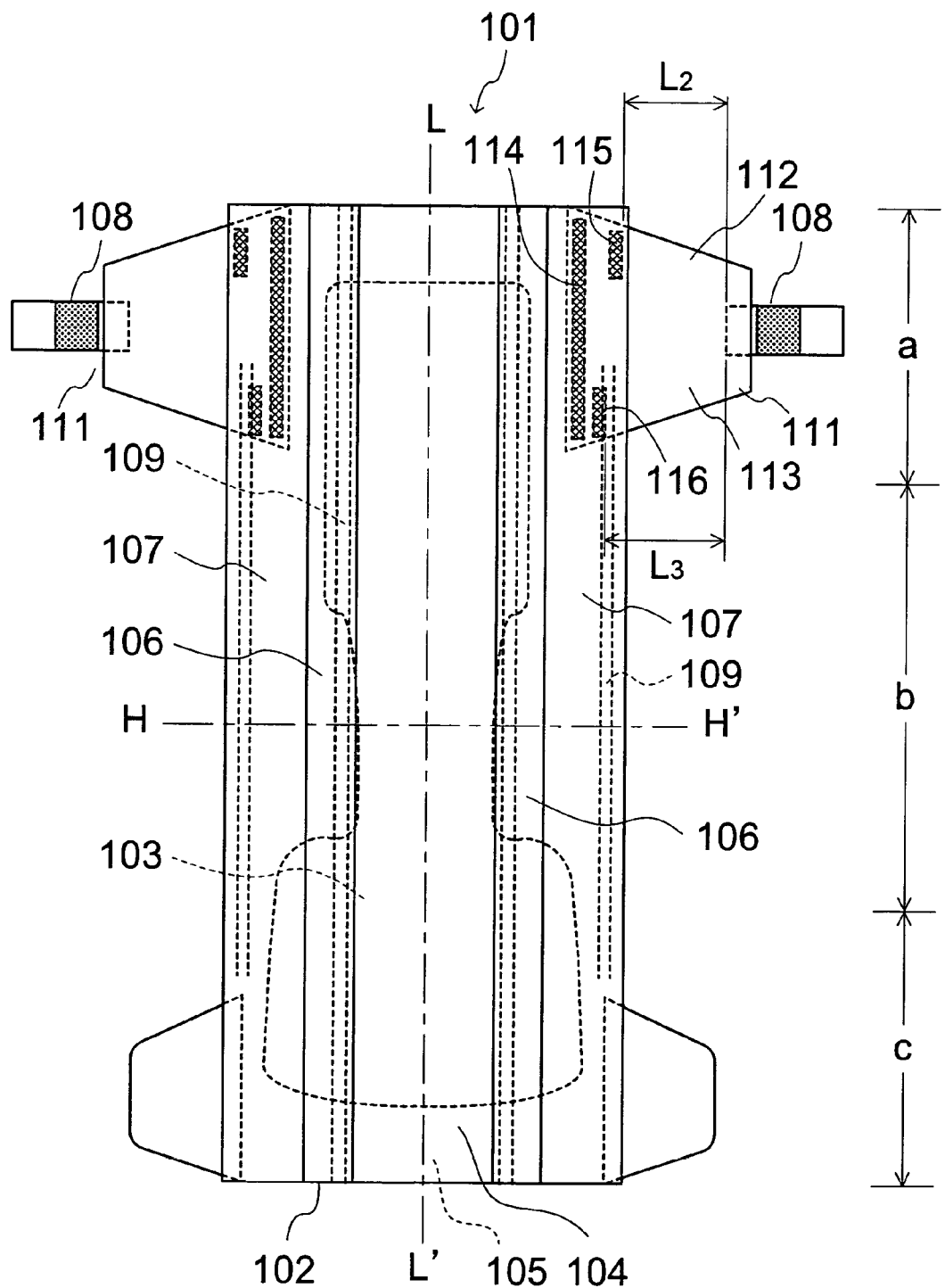
FIG. 18 is a developed view of the eighth embodiment according to the present invention where a body side face (face in contact with the skin of a wearer) is directed toward an observer.
Figure 19:
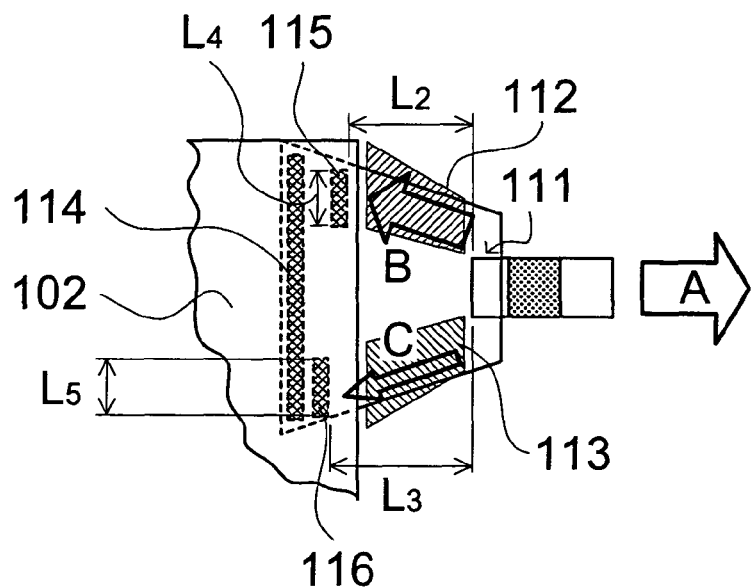
FIG. 19 is an enlarged partial front view showing distribution of the tensile force when the fastener of the disposable diaper is pulled according to the eighth embodiment of the present invention.

FIG. 18 is a developed view of the eighth embodiment related to this invention, with the side of the body (surface contacting the skin of a wearer) directed toward the observer, and FIG. 19 is a view showing behavior of the tensile force when the fastener means is pulled for the disposable diaper of the eighth embodiment. In the embodiments given below, configurations which are the same as those shown in the second embodiment are given the same symbols to omit overlapping descriptions.

The eighth embodiment is similar to the foregoing seventh embodiment but reverse in the locations at which the joint parts 115 and 116 of the side flap 111 installed along longitudinal end parts of the diaper body 102 are provided. More particularly, as illustrated in FIG. 18, the first joint part 115 of the side flap 111 is provided outside the width direction of the diaper body 102 (direction of horizontal centerline H-H') and at the side edge of the diaper body 102 and the second joint part 116 is provided outside the side flap fixing part 114 and in the vicinity of the side flap fixing part 114.

As with the second embodiment, this disposable diaper 101 is also provided with the first waist area "a" and groin area "b" as well as the second waist area "c", and composed of the diaper body 102, a pair of side flaps 111 extending in the width direction of the diaper body 102 (direction of horizontal centerline H-H' in the figure) at the first waist area "a" and in the vicinity of the longitudinal end part and a pair of fasteners 8 installed on the side edges of the respective side flaps 111.

The diaper body 102 is composed of the liquid permeable top sheet 104 coming into contact with the skin of a wearer, the liquid impermeable back sheet 105 comprising the side of garment, the absorbent body 103 contained inside these sheets and being approximately rectangular and hourglass-formed and the like as a whole, steric gathers 106 installed on the surface of top sheet 104 approximately at both side parts of this absorbent body 103, and the elastic members 109 provided along the longitudinal direction of the steric gathers 106 (direction of longitudinal center line L-L' in the figure) and imparting elasticity to the steric gathers 106. The top sheet 104 and the back sheet 105 are greater in length and width than the absorbent body 103, extending outside beyond the edge of the absorbent body 103, forming the leg gathers 107 at least at the groin area "b" and provided with the elastic members 109 for imparting elasticity to the leg gathers 107.

Also, the side flaps 111 are positioned at the ventral side (first waist area "a") of the diaper body 102 as separated members not as members contiguous with the diaper body 102. These may be positioned at the dorsal side (second waist area "c").

The side flap 111 is fixed with the diaper body 102 at the side flap fixing part 114. The side flap 111 is also joined with the diaper body 102 at two sites, namely, at the side edge upper end area 112 and the side edge lower end area 113, respectively forming the first joint part 115 and the second joint part 116. The first joint part 115 and the second joint part 116 of the side flap 111 are provided apart from each other in the longitudinal direction of the disposable diaper 101 (direction of longitudinal center line L-L'), and at the same time, the first joint part 115 of the side flap 111 is located outside the width direction of the diaper body 102 (direction of horizontal center line H-H') and at the side edge of the diaper body 102 and the second joint part 116 of the side flap 111 is located outside the side flap fixing part 114 and in the vicinity of the side flap fixing part 114. More particularly, a configuration is given so that the effective length $L_2$ between the first joint part 115 of the side flap 111 and the fastener means 108 is shorter than the effective length $L_3$ between the second joint part 116 of the side flap 111 and the fastener means 108.

Additionally, this side flap 111 is installed so as to be sandwiched between the top sheet 104 and the back sheet 105, and may be installed on the surface of the back sheet 105 of the diaper body 102 (opposite to the body and on the side of a garment). Further, the method for joining the side flap 111 with the diaper body 102 and the location of the side flap fixing part 114 and materials used for the members comprising the disposable diaper 101 are the same as those given in the second embodiment, and overlapping descriptions are omitted.

Next, behavior of the tensile force when the fastener means 108 is pulled for the disposable diaper 101 in this eighth embodiment is described based on FIG. 19.

As illustrated in FIG. 18 and FIG. 19, in the disposable diaper 101 of the present invention, the side flap 111 is fixed with the diaper body 102 at the side flap fixing part 114 and the side flap 111 is also joined with the diaper body 102 at two sites, namely, at the side edge upper end area 112 and the side edge lower end area 113, respectively, forming the first joint part 115 and the second joint part 116 of the side flap 111. The first joint part 115 and the second joint part 116 of the side flap 111 are provided apart from each other in the longitudinal direction of the disposable diaper 101 (direction of longitudinal center line L-L'), at the same time, the first joint part 115 of the side flap 111 is located outside the width direction of the diaper body 102 (direction of horizontal centerline H-H') and at the side edge of the diaper body 102 and the second joint part 116 of the side flap 111 is located outside the side flap fixing part 114 and in the vicinity of the side flap fixing part 114. More particularly, as illustrated in FIG. 19, a configuration is given where the effective length $L_2$ between the first joint part 115 of the side flap 111 and the fastener means 108 is shorter than the effective length $L_3$ between the second joint part 116 of the side flap 111 and the fastener means 108. In this configuration, as illustrated in FIG. 19, the tensile force A given to the fastener means 108 is divided into force B interlocking with the side edge upper end area 112 of the side flap 111 and force C interlocking with the side edge lower end area 113 of the side flap 111 in such a fashion that the force B interlocking with the side edge upper end area 112 of the side flap 111 is greater than the force C interlocking with the side edge lower end area 113 of the side flap 111, thus respectively acting on the first joint part 115 and the second joint part 116.

Therefore, the tensile force A given to the fastener means 108 imparts actions so that that areas around the waist are more effectively and intensively pulled than areas around the legs, thus resulting in a better fitness at areas around the waist of the wearer.

Figure 20:
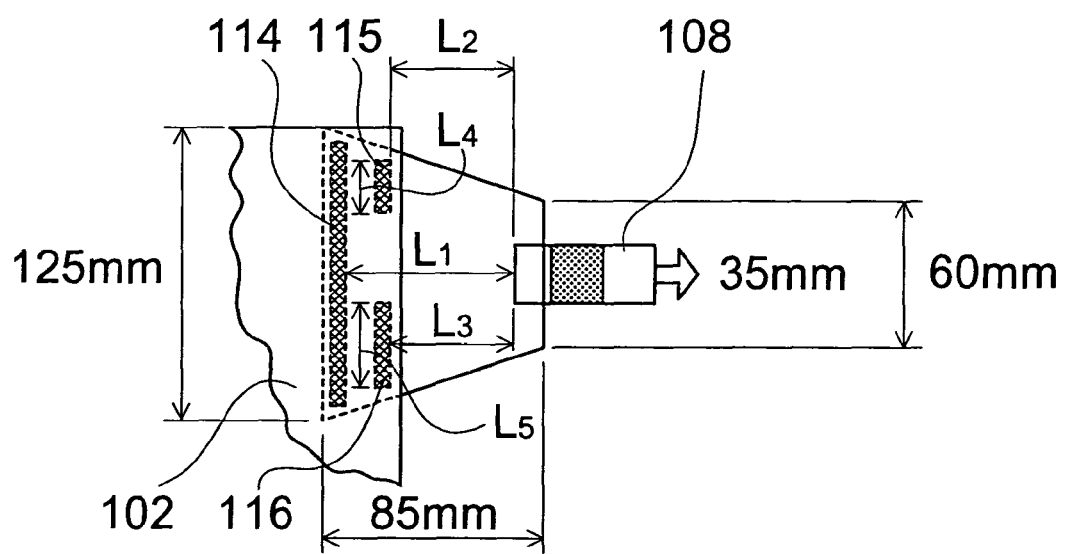
FIG. 20 is a schematic view showing a shape of samples.

Next, measurements were made for the effective lengths $L_1$, $L_2$ and $L_3$ between the side flap fixing part 114, joint parts 115 and 116 which fix or join the side flap 111 to the diaper body 102 and the fastener means 108 as well as the respective lengths $L_4$ and $L_5$ of these joint parts 115 and 116, and evaluation was made for the interrelationship with the tensile force acting on respective areas. FIG. 20 is a view illustrating the configuration of samples.

Test Method

Samples: As illustrated in FIG. 20, approximately trapezoid-shaped side flap 111 having an upper side length of 60 mm, a lower side length of 125 mm and a height of 85 mm was fixed with the diaper body 102 at the lower side of the side flap to form the side flap fixing part 114 and fixed with the fastener means 108 at the upper side thereof, thus preparing the samples. Locations and lengths of the joint parts 115 and 116 of the side flap 111 were designed on the basis of the specifications of the samples given in Table 1 to prepare 5 types of samples.

Measurement method: The fastener means 108 and the side flap fixing part 114 were held by a chuck (chuck distance of 50 mm) and the side flap 111 was pulled at a rate of 100 mm/minute until 35 mm of the stretched length (corresponding to about a 70% extension in relation to the effective length of $L_1$) was obtained to measure the tensile force at this point in time (hereinafter referred to as maximum point stress). This test was carried out two times repeatedly for each sample to measure the maximum point stress for the second test.

Measuring equipment: Autograph model AGS-1k NG (Shimadzu Corporation, Kyoto, Japan)

Test Results and Evaluation

Table 1 shows the test results, demonstrating that the tensile force pulled by the fastener means 108 imparted stress different to the side edge upper end area or the side edge lower end area of the side flap 111, due to the fact that the effective lengths $L_2$ and $L_3$ between the joint parts 115 and 116 of the side flap 111 and the fastener means 108 were different from the lengths $L_4$ and $L_5$ of these joint parts 115 and 116 of the side flap 111. The following is an explanation regarding the test results of individual samples and the evaluation thereof.

TABLE 1

|  |  | Sample 1 | Sample 2 | Sample 3 | Sample 4 | Sample 5 |
|---|---|---|---|---|---|---|
| Specification of Samples | L1: Effective length between the fastner means 108 and the side flap fixing part (mm) | 50 | 35 | 50 | 50 | 50 |
|  | L2: Effective length between the fastner means 108 and the first joint part 115 (mm) | — | — | 35 | 35 | 35 |
|  | L3: Effective length between the fastner means 108 and the second joint part 116 (mm) | — | — | 35 | 35 | — |
|  | L4: Length the first joint part 115 | No joint part | No joint part | 15 | 5 | 15 |
|  | L5: Length the second joint part 116 | No joint part | No joint part | 15 | 5 | No joint part |
| Maximum Point Stress | the second cycle (N) | 22.6 | 30.4 | 29.5 | 24.8 | 28.6 |

1) The samples 1 and 2 are those devoid of the first joint part 115 and the second joint part 116 of the side flap 111, and the effective length $L_1$ between the fastener means 108 and the side flap fixing part 114 is 50 mm for sample 1 and 35 mm for sample 2. In this instance, the respective maximum point stresses at 35 mm of the stretched length are 22.6 N and 30.4 N as shown in Table 1. This finding has revealed that the shorter the effective length $L_1$ between the fastener means 108 and the side flap fixing part 114, the greater the maximum point stress becomes.

2) Sample 3 is a sample where the joint parts 115 and 116 of the side flap 111 are provided at the side edge upper end area and side edge lower end area of the side flap 111, with the lengths $L_4$ and $L_5$ set at 15 mm, respectively. The effective lengths $L_2$ and $L_3$ between the fastener means 108 and the joint parts 115 and 116 of the side flap 111 are respectively 35 mm, and the effective length $L_1$ between the fastener means 108 and the side flap fixing part 114 is 50 mm. Sample 3 provides 29.5 N of the maximum point stress at 35 mm of the stretched length, imparting 6.9 N of the stress, which is equal to (maximum point stress of 29.5 N in the sample 3) minus (maximum point stress of 22.6 N in the sample 1), effectively and intensively to the areas given in FIG. 6 of the second embodiment (corresponding to areas around the waist and legs of a wearer).

3) Sample 4 is similar to sample 3 but different in that the lengths $L_4$ and $L_5$ of the joint parts 115 and 116 of the side flap 111 are given 5 mm, that is, the lengths of the joint part 115 and 116 are shortened. Sample 4 provides 24.8 N of the maximum point stress at 35 mm of the stretched length, imparting 2.2 N of the stress, which is equal to (maximum point stress 24.8 N in the sample 4) minus (maximum point stress 22.6 N in the sample 1), effectively and intensively to the areas given in FIG. 6 of the second embodiment (corresponding to areas around the waist and legs of a wearer).

These samples 3 and 4 have demonstrated that an arbitrary change in the lengths $L_4$ and $L_5$ of the joint parts 115 and 116 of the side flap 111 is able to control the stress given to areas around the waist and legs of a wearer. More particularly, as explained in the foregoing fourth and fourth embodiments, by making the length $L_4$ of the first joint part 115 of the side flap 111 different from the length $L_5$ of the second joint part 116 of the side flap 111, a different fitness to the areas around the waist and legs of the wearer is achieved.

4) Sample 5 is similar to sample 3 but different in that the second joint part 116 of the side flap 111 is removed (corresponding to the fifth embodiment). Sample 5 provides 28.6 N of the maximum point stress at 35 mm of the stretched length, imparting intensively 6.0 N of the stress, which is equal to (maximum point stress 28.6 N in the sample 5) minus (maximum point stress 22.6 N in the sample 1), only to the side edge upper end area of the side flap 111.

In other words, as explained in the foregoing sixth and sixth embodiments, where the joint parts 115 and 116 of the side flap 111 are located either at the side edge upper end area or at the side edge lower end area of the side flap 111, tensile force acts intensively on areas having the joint part 115 and 116 of the side flap 111.

Further, a change in the length and location of the first joint part and the second joint part of the side flap is able to control fitness around the waist and legs. For example, where the length of the first joint part of the side flap is made longer than the second joint part, a better fitness can be obtained around the waist rather than around the legs. Further, where the first joint part of the side flap is located outside the diaper body in relation to the second joint part of the side flap, a better fitness is obtained around the waist rather than around the legs. Thus, fitness around the waist and legs can be arbitrarily controlled by appropriately selecting the joint parts of the side flap.

As explained above, the disposable diaper related to the present invention was explained specifically by referring to illustrative figures. This invention shall not be construed to be limited to the illustrated embodiments but may be changed appropriately for executing the present invention as long as the change does not deviate from the purpose of the present invention. Such a change may be included in the technical scope of the present invention. For example, a change may be made both in the length and location of the first joint part and the second joint part of the side flap, or others.

The invention claimed is:
1. A disposable diaper, comprising:
   a diaper body having a top sheet, a back sheet, and an absorbent body enclosed between the top sheet and the back sheet;
   a pair of side flaps fixed to the diaper body; and
   a pair of fasteners;
   wherein the diaper body further has a pair of side edges extending in a longitudinal direction of the diaper body;
   wherein each of the side flaps extends in a width direction of the diaper body and has an inner end being disposed inboard of a respective one of the side edges of the diaper body and an outer end being disposed outboard of the respective side edge of the diaper body, and each of the fasteners is fixed to the outer end of one of the side flaps; and
   wherein each of the side flaps is fixed to the diaper body at
      a fixing part being arranged adjacent and along an inner edge of the inner end of the respective side flap,
      a first joint part located at an upper part of the inner end of the respective side flap, and
      a second joint part located at a lower part of the inner end of the respective side flap, the lower part being spaced in the longitudinal direction from the upper part, and the fixing part being spaced, in the width direction of the diaper body, from the joint parts by a bonding-free region in which the side flap is free of direct attachment to the diaper body; and
   wherein a pulling force, which occurs when the fastener fixed to each of the side flaps is pulled transversely outwardly in use, is dispersed into first and second tensile forces directed towards the first and second joint parts, respectively, and concentrated around leg and waist openings of the diaper for enhanced fit of the diaper on a wearer in use.

2. The disposable diaper according to claim 1, wherein the first joint part and the second joint part have a same length, as measured in the longitudinal direction.

3. The disposable diaper according to claim 1, wherein each the side flap comprises an elastic sheet and a non-woven fabric.

4. The disposable diaper according to claim 1, wherein each the fastener is positioned at a substantial center, as seen in the longitudinal direction, of the outer end of the respective side flap.

5. The disposable diaper according to claim 1, wherein each the side flap is fixed to the diaper body at the first and second joint parts and the fixing part by thermal bonds.

6. The disposable diaper according to claim 1, wherein each the fastener comprises a fastening member and a tape substrate.

7. The disposable diaper according to claim 1, wherein a length of the first joint part, as measured in the longitudinal direction, is shorter than that of the second joint part.

8. The disposable diaper according to claim 1, wherein a length of the first joint part, as measured in the longitudinal direction, is longer than that of the second joint part.

9. The disposable diaper according to claim 1, wherein each the side flap comprises an elastic sheet.

10. The disposable diaper according to claim 3, wherein the non-woven fabric is elastic.

11. A method of adjusting fitting of a disposable diaper about a waist and legs of a wearer when the disposable diaper is worn, the disposable diaper comprising a diaper body and a side flap fixed to the diaper body;
   wherein an inner end of the side flap is fixed to an inner portion of the diaper body, and either or both of a side edge upper end area and a side edge lower end area of the side flap are joined to the diaper body at an outer portion of the diaper body, the outer portion being spaced in a width direction of the diaper body from the inner portion;

the method comprising:

adjusting at least one of (i) lengths and (ii) widths of a first joint part, at which the side edge upper end area of the side flap is joined to the outer portion of the diaper body, and a second joint part, at which the side edge lower end of the side flap is joined to the outer portion of the diaper body; and fixing a fastener to an outer end of the side flap in a region which extends outwardly in the width direction from a bonding-free region of the side flap, wherein the side flap is free of direct attachment to the diaper body in the bonding-free region, and wherein the first and second joint parts are spaced from each other in a longitudinal direction of the diaper body by the bonding-free region.

12. A method of adjusting fitting of a disposable diaper about a waist and legs of a wearer when the disposable diaper is worn, the disposable diaper comprising a diaper body and a side flap fixed to the diaper body;

wherein an inner end of the side flap is fixed to an inner portion of the diaper body, and either or both of a side edge upper end area and a side edge lower end area of the side flap are joined to the diaper body at an outer portion of the diaper body, the outer portion being spaced in a width direction of the diaper body from the inner portion;

the method comprising:

adjusting respective positions of a first joint part at which the side edge upper end area of the side flap is joined to the outer portion of the diaper body, and a second joint part at which the side edge lower end of the side flap is joined to the outer portion of the diaper body; and fixing a fastener to an outer end of the side flap in a region which extends outwardly in the width direction from a bonding-free region of the side flap, wherein the side flap is free of direct attachment to the diaper body in the bonding-free region, and wherein the first and second joint parts are spaced from each other in a longitudinal direction of the diaper body by the bonding-free region.

13. The disposable diaper according to claim 1, wherein one of the first and second joint parts is closer to the respective side edge of the diaper body than the other.

14. The disposable diaper according to claim 1, wherein the fixing part extends continuously along substantially an entire length, as measured in the longitudinal direction, of the inner edge of the inner end of the respective side flap, and a length, as measured in the longitudinal direction, of each of the first and second joint parts is shorter than half of that of the fixing part.

15. The disposable diaper according to claim 1, further comprising:

leg elastic elements extending in the longitudinal direction and along the side edges of the diaper body;

wherein the second joint part of each the side flap overlaps at least one of the leg elastic elements.

16. The disposable diaper according to claim 15, wherein the first joint part of each the side flap is located on an imaginary extension of said at least one of the leg elastic elements but does not overlap any of the leg elastic elements.

17. A disposable diaper, comprising:

a diaper body having a top sheet, a back sheet, and an absorbent body enclosed between the top sheet and the back sheet;

a pair of side flaps fixed to the diaper body; and a pair of fasteners;

wherein the diaper body further has a pair of side edges extending in a longitudinal direction of the diaper body;

wherein each of the side flaps extends in a width direction of the diaper body and has an inner end being disposed inboard of a respective one of the side edges of the diaper body and an outer end being disposed outboard of the respective side edge of the diaper body, and each of the fasteners is fixed to the outer end of one of the side flaps;

wherein each of the side flaps is fixed to the diaper body at a fixing part being arranged adjacent and along an inner edge of the inner end of the respective side flap, a first joint part located at an upper part of the inner end of the respective side flap, and a second joint part located at a lower part of the inner end of the respective side flap, the fixing part being spaced, in the width direction of the diaper body, inwardly from the joint parts by a bonding-free region in which the side flap is free of direct attachment to the diaper body, and the second joint part being spaced in the longitudinal direction from the first joint part by a section of the bonding-free region; and wherein each of the fasteners is disposed such that the fastener is not co-elevational in the longitudinal direction with any portion of the first joint part and the second joint part.

18. The disposable diaper according to claim 17, wherein each of the fasteners is disposed such that an entirety of the fastener is co-elevational in the longitudinal direction with the bonding-free region's section that separates the first and second joint parts in the longitudinal direction; and wherein a pulling force, which occurs when the fastener fixed to each of the side flaps is pulled transversely outwardly in use, is dispersed into first and second tensile forces directed towards the first and second joint parts, respectively, and concentrated around leg and waist openings of the diaper for enhanced fit of the diaper on a wearer in use.

19. The disposable diaper according to claim 18, wherein each of the side flaps extends continuously in the longitudinal direction from the first joint part, across the bonding-free region's section that separates the first and second joint parts, and to the second joint part, without being interrupted by any bonding line or edge of the side flap.

* * * * *